US012661358B2

(12) United States Patent
Mabondzo et al.

(10) Patent No.: US 12,661,358 B2

(45) Date of Patent: Jun. 23, 2026

(54) PURINE DERIVATIVES AS DRUGS FOR THE TREATMENT OF NEONATAL HYPOXIA-ISCHEMIA BRAIN INJURY AND RELATED DISEASES

(71) Applicants: COMMISSARIAT A L'ENERGIE ATOMIQUE ET AUX ENERGIES ALTERNATIVES, Paris (FR); WOMEN & INFANTS HOSPITAL OF RHODE ISLAND, Providence, RI (US); SCIENTIAM PHARMA, Paris (FR)

(72) Inventors: Aloïse Mabondzo, Paris (FR); Anne-Cécile Guyot, Rueil Malmaison (FR); Alain Pruvost, Gif sur Yvette (FR); Narciso Costa, Saulx-les-Chartreux (FR); Hervé Galons, Paris (FR); Nassima Oumata, Roscoff (FR); Barbara Stonestreet, Providence, RI (US); Clémence Disdier, Gif sur Yvette (FR)

(73) Assignees: COMMISSARIAT A L'ENERGIE ATOMIQUE ET AUX ENERGIES ALTERNATIVES, Paris (FR); WOMEN & INFANTS HOSPITAL OF RHODE ISLAND, Providence, RI (US); SCIENTIAM PHARMA, Paris (FR)

( * ) Notice: Subject to any disclaimer, the term of this patent is extended or adjusted under 35 U.S.C. 154(b) by 755 days.

(21) Appl. No.: 17/920,969

(22) PCT Filed: Apr. 23, 2021

(86) PCT No.: PCT/EP2021/060719

§ 371 (c)(1),
(2) Date: Oct. 24, 2022

(87) PCT Pub. No.: WO2021/214315

PCT Pub. Date: Oct. 28, 2021

(65) Prior Publication Data

US 2023/0181592 A1 Jun. 15, 2023

(30) Foreign Application Priority Data

Apr. 23, 2020 (EP) .................................... 20315215

(51) Int. Cl.

| | |
|---|---|
| ***A61K 31/52*** | (2006.01) |
| ***A61K 31/522*** | (2006.01) |
| ***A61P 25/00*** | (2006.01) |
| ***C07D 473/04*** | (2006.01) |
| ***C07D 473/16*** | (2006.01) |
| ***C07D 473/18*** | (2006.01) |

(52) U.S. Cl.

CPC ............. *A61K 31/52* (2013.01); *A61P 25/00* (2018.01)

(58) Field of Classification Search

CPC .... A61K 31/52; A61K 31/522; C07D 473/04; C07D 473/16; C07D 473/18; A61P 25/00

See application file for complete search history.

(56) References Cited

FOREIGN PATENT DOCUMENTS

| | | | |
|---|---|---|---|
| EP | 1 444 982 | A1 | 8/2004 |
| EP | 2 664 619 | A1 | 11/2013 |
| WO | 2004/016612 | A2 | 2/2004 |
| WO | 2018/189122 | A1 | 10/2018 |

OTHER PUBLICATIONS

Jun. 25, 2021 International Search Report issued in International Patent Application No. PCT/EP2021/060719.

Sep. 16, 2020 Extended European Search Report issued in European Patent Application No. 20315215.2.

D. Ukena et al., "N6-substituted 9-methyladenines: a new class of adenosine receptor antagonists", FEBS Letters, Elsevier Science Publishers B. V. (Biomedical Division), vol. 215, No. 2, (1987), pp. 203-208.

Pier Giovanni Baraldi et al., "An efficient one-pot synthesis of 6-alkoxy-8,9-dialkylpurines via reaction of 5-amino-4-chloro-6-alkylaminopyrimidines with N,N-dimethylalkaneamides and alkoxide ions", Tetrahedron 58 (2002), pp. 7607-7611.

Jun. 25, 2021 Written Opinion issued in International Patent Application No. PCT/EP2021/060719.

Lin Tang et al., "Crystal Structure of Pyridoxal Kinase in Complex with Roscovitine and Derivatives", The Journal of Biological Chemistry, vol. 280, No. 35, (2005), pp. 31220-31229.

Seetha Shankaran et al., "Childhood Outcomes after Hypothermia for Neonatal Encephalopathy", The New England Journal of Medicine 366; 22, (2012), pp. 2085-2092.

(Continued)

*Primary Examiner* — Bruck Kifle

(74) *Attorney, Agent, or Firm* — Oliff PLC

(57) ABSTRACT

A compound of formula (I), for use in the treatment of non-traumatic acquired brain injury, (I)

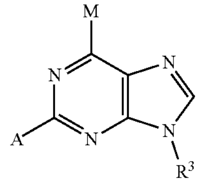

in which M represents a $NR^1R^2$ group, an $OR^1$ group or a $SR^1$ group, A represents a $NR^4R^5$ group, an $OR^{10}$ group or a hydrogen atom, $R^3$ is a $(C_1\text{-}C_6)$alkyl group, a $(C_1\text{-}C_6)$ cycloalkyl group, an aryl group, a $—CH_2$-aryl group, a $CH_2$-$(C_1\text{-}C_6)$cycloalkyl group or a $—CH_2$-heteroaryl group, and its addition salts with pharmaceutically acceptable acids. A compound of formula (I) wherein $R^5$ is a $(C_1\text{-}C_8)$ alkyl group or a $(C_1\text{-}C_6)$cycloalkyl group, said alkyl and cycloalkyl group being substituted with one, two or three $—OCOR^a$ group(s).

9 Claims, 4 Drawing Sheets

(56) References Cited

OTHER PUBLICATIONS

V. Riljak et al., "Pathophysiology of Perinatal Hypoxic-Ischemic Encephalopathy-Biomarkers, Animal Models and Treatment Perspectives", Physiological Research 65 (Suppl. 5), (2016), pp. S533-S545.
Karen S. Mark et al., "Cerebral microvascular changes in permeability and tight junctions induced by hypoxia-reoxygenation", Am J Physiol Heart Circ Physiol 282, (2002), pp. H1485-H1494.
G. J. Del Zoppo, "Inflammation and the Neurovascular Unit in the Setting of Focal Cerebral Ischemia", Neuroscience 158 (2009) pp. 972-982.
X. Chen et al., "Ischemia-Reperfusion Impairs Blood-Brain Barrier Function and Alters Tight Junction Protein Expression in the Ovine Fetus", Neuroscience 226 (2012), pp. 89-100.
Giuseppe Buonocore et al., "New Pharmacological Approaches in Infants with Hypoxic-Ischemic Encephalopathy", Current Pharmaceutical Design, (2012), 18, pp. 3086-3100.
Helen M. Bramlett et al., "Pathophysiology of cerebral ischemia and brain trauma: Similarities and differences", Journal of Cerebral Blood Flow & Metabolism 24, (2004), pp. 133-150.

PURINE DERIVATIVES AS DRUGS FOR THE TREATMENT OF NEONATAL HYPOXIA-ISCHEMIA BRAIN INJURY AND RELATED DISEASES

FIELD OF THE INVENTION

The present invention aims at providing purine derivatives, which are Aftins, for use in the treatment of non-traumatic Acquired Brain Injuries (ABI), in particular in the treatment of hypoxic injuries, and more particularly in the treatment of neonatal hypoxia-ischemia (HI) and neonatal hypoxic-ischemic encephalopathy (HIE).

BACKGROUND OF THE INVENTION

Acquired brain injuries (ABI) define brain damage caused by events occurring before or after birth, i.e. not hereditary, congenital, degenerative or induced by birth related injury. Brain damage commonly encompassed within said definition are non-progressive cerebral lesions, typically produced by ischemic, anoxic, hemorrhagic, infectious events and non-malignant tumors. ABI can result in cognitive, physical, emotional, or behavioral impairment that lead to permanent or temporary changes such as physical effects, changes in thinking or learning abilities, changes with the management of behavior or emotions. Rehabilitation of ABI generally takes time. Although the biggest improvements usually come in the first few months after injury, recovery can continue for years afterwards.

As a more specific type of non-traumatic ABI, as will be developed herein after, neonatal brain injuries may be cited. They are one of the leading causes of infant mortality and long-term neurologic disability, such as developmental disabilities including mental retardation and cerebral palsy which create a large burden on society, highlighting the urgent need for effective neuroprotective strategies to reduce the prevalence of brain injuries.

In particular, hypoxia-ischemia (HI) and hypoxic-ischemic encephalopathy (HIE) represent common causes of neurological injury in preterm and full-term infants with birth related complications.

There is no pharmacological treatment currently available to provide protection against brain injury in neonates. Hypothermia is the only approved therapy for HIE, but it can only be used to treat full term infants, and is only partially protective (Buonocore, G., et al., New Pharmacological Approaches in Infants with Hypoxic-Ischemic Encephalopathy, *Current Pharmaceutical Design,* 2012. 18(21): p. 3086-3100; Shankaran, S., Childhood Outcomes after Hypothermia for Neonatal Encephalopathy, *New England Journal of Medicine,* 2012. 366(22): p. 2085-2092. Indeed, almost half of infants treated with hypothermia still die or suffer from long-lasting neurological impairment.

Hence, there is an urgent need for new therapeutic options to treat non-traumatic ABIs, and in particular to treat HI and HIE.

Further, a large number of in vitro and in vivo studies have documented increased BBB (Blood-brain barrier) permeability with alterations in the expression and localization of key tight junction (TJ) components after HI in neonates (Mark, K. S. and T. P. Davis, Cerebral microvascular changes in permeability and tight junctions induced by hypoxia-reoxygenation, *American Journal of Physiology-Heart and Circulatory Physiology,* 2002. 282(4): p. H1485-H1494.21; Chen, X., et al., Ischemia-reperfusion impairs blood-brain barrier function and alters tight junction protein expression in the ovine fetus, *Neuroscience,* 2012. 226: p. 89-100).

The BBB is the cellular structure that separates the brain parenchyma from the bloodstream. The endothelium has very specific properties that enable it to regulate exchanges between the blood and the brain parenchyma. The BBB is comprised of a specialized monolayer of brain endothelial cells, pericytes, and astrocyte "end feet". Early in development, well-formed tight junctions (TJs) between brain endothelial cells have been shown to constitute the physical basis for effective barrier mechanism(s) and are crucial to establish a stable brain environment needed for a proper brain maturation. Most alterations in the BBB are observed early (hours to days) after exposure to an HI insult. HI-induced BBB opening significantly contributes to neuronal cell death.

Therefore, the inventors identified the BBB as an important potential target to decrease and/or repair brain lesions after HI injury.

Aftins are a family of tri-substituted purines that are chemically synthetized. This family of compounds was originally designed for a non-therapeutic approach as disclosed in EP2 664 619 and are now known from WO2018/189122 as being useful in the treatment of neurodegenerative disorders, such as Alzheimer's disease (AD). As disclosed in WO2018/189122, in murine in vivo models of AD and ex vivo on hippocampal organotypic slide cultures, neurotrophic markers were increased and pro-inflammatory cytokines expression were decreased after Aftin administration. Improvement in cognitive tests was also demonstrated in adult mice model of neuro-inflammation.

However, to the inventors' knowledge, it has never been suggested or demonstrated in the prior art that Aftins could repair and/or decrease brain injury lesions, in particular in patients suffering from acquired brain injuries (ABI).

SUMMARY OF THE INVENTION

It has now been found that Aftin compounds, and in particular the compound of formula (I) as defined herein after, are useful in the treatment of acquired brain injuries (ABI), in particular in brain injuries caused by oxygen deficiency, and even more particularly in hypoxic injuries such as neonatal encephalopathy, including neonatal hypoxia-ischemia and neonatal hypoxic-ischemic encephalopathy.

The present invention therefore relates to compounds of formula (I) as defined below for use in treating non traumatic acquired brain injuries (ABI), in particular in brain injuries caused by oxygen deficiency, and even more particularly in hypoxic injuries such as neonatal encephalopathy, including neonatal hypoxia-ischemia and neonatal hypoxic-ischemic encephalopathy.

The present invention further relates to a subclass of compounds of formula (I), as defined below and which is new.

From left to right: Sham group (non-treated control group), HI+PL group (HI injury induced+no active agent administered), and HI+Compound 13 (HI injury induced+compound 13 administered).

Figure 1A:
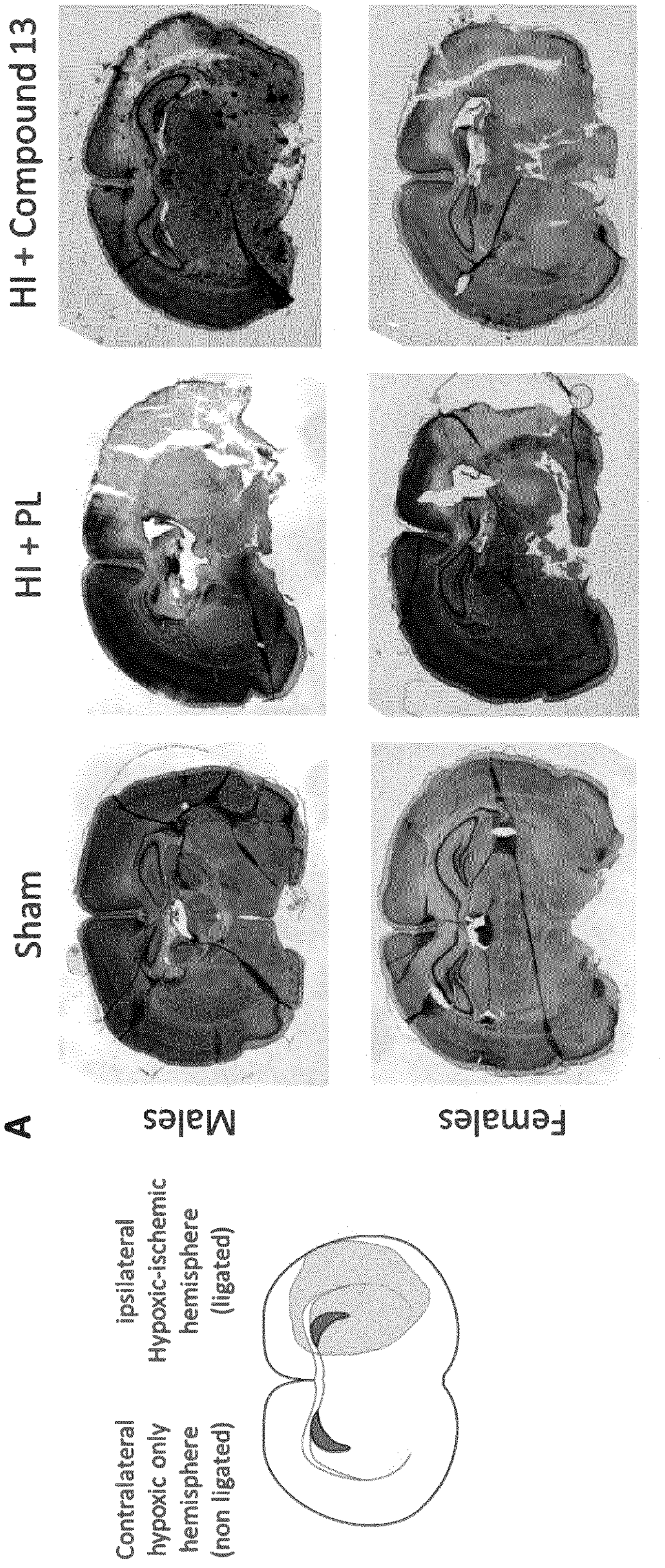
FIG. 1A: Representative images of brain slices stained with cresyl violet 3 days after HI brain injury. Top row: brain slices from male rats; bottom row: brain slices from female rats.
Figure 1B:
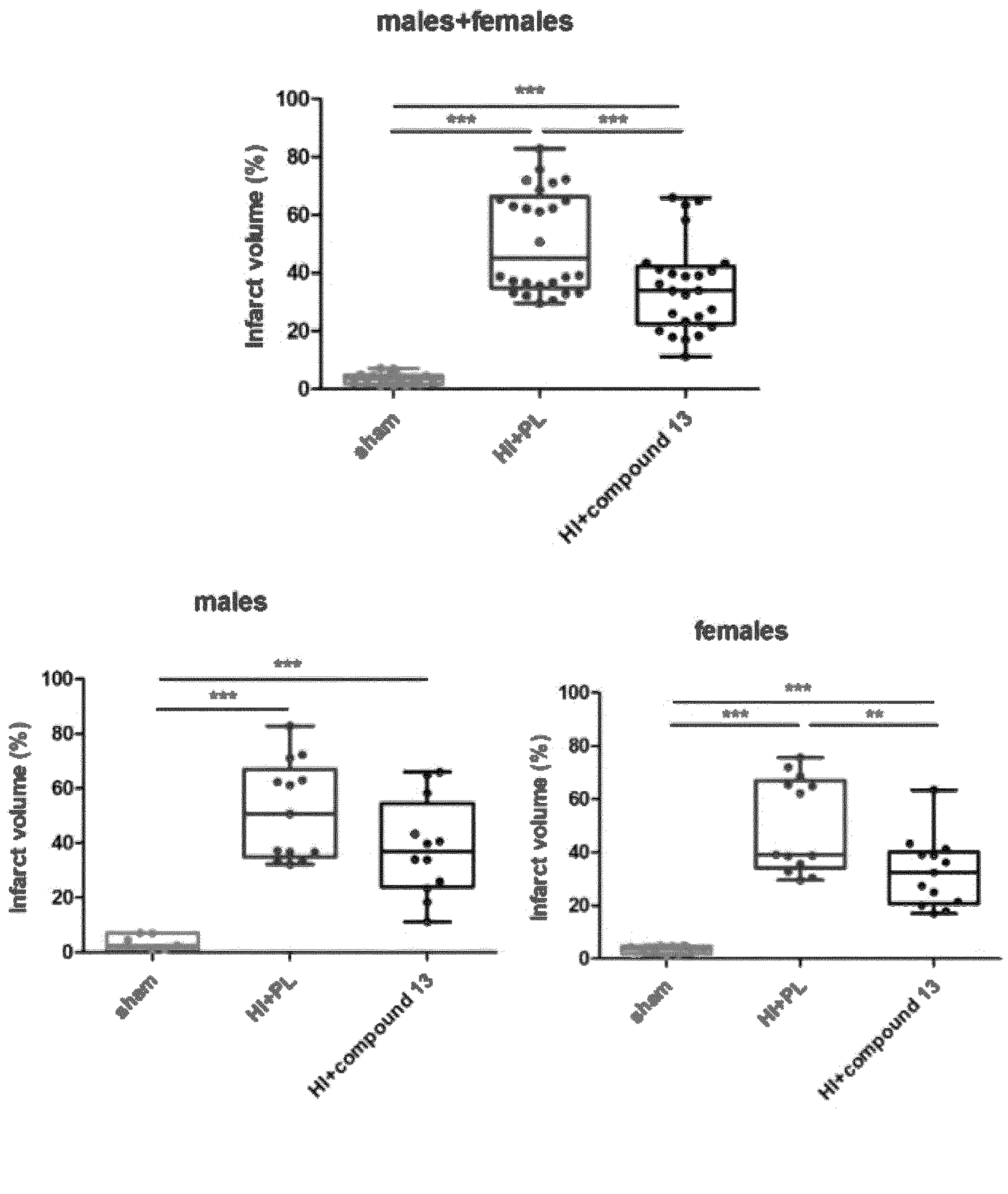
FIG. 1: Ability of Aftin to decrease the infarct volume of the hemisphere ipsilateral to HI (Hypoxia-Ischemia) injury in the Rice Vannucci model.

FIG. 1B: Infarct volume (%) measured for each of the studied groups. y-axis: infarct volume (%); x-axis (from left to right): Sham, HI+PL, and HI+compound 13 groups.

From left to right: graphic results for males+females, graphic results for males alone and graphic results for females alone.

Sham: male n=5, female n=10;

HI+PL: male n=8, female n=8;

HI+compound 13: male n=7, female n=6.

Figure 2A:
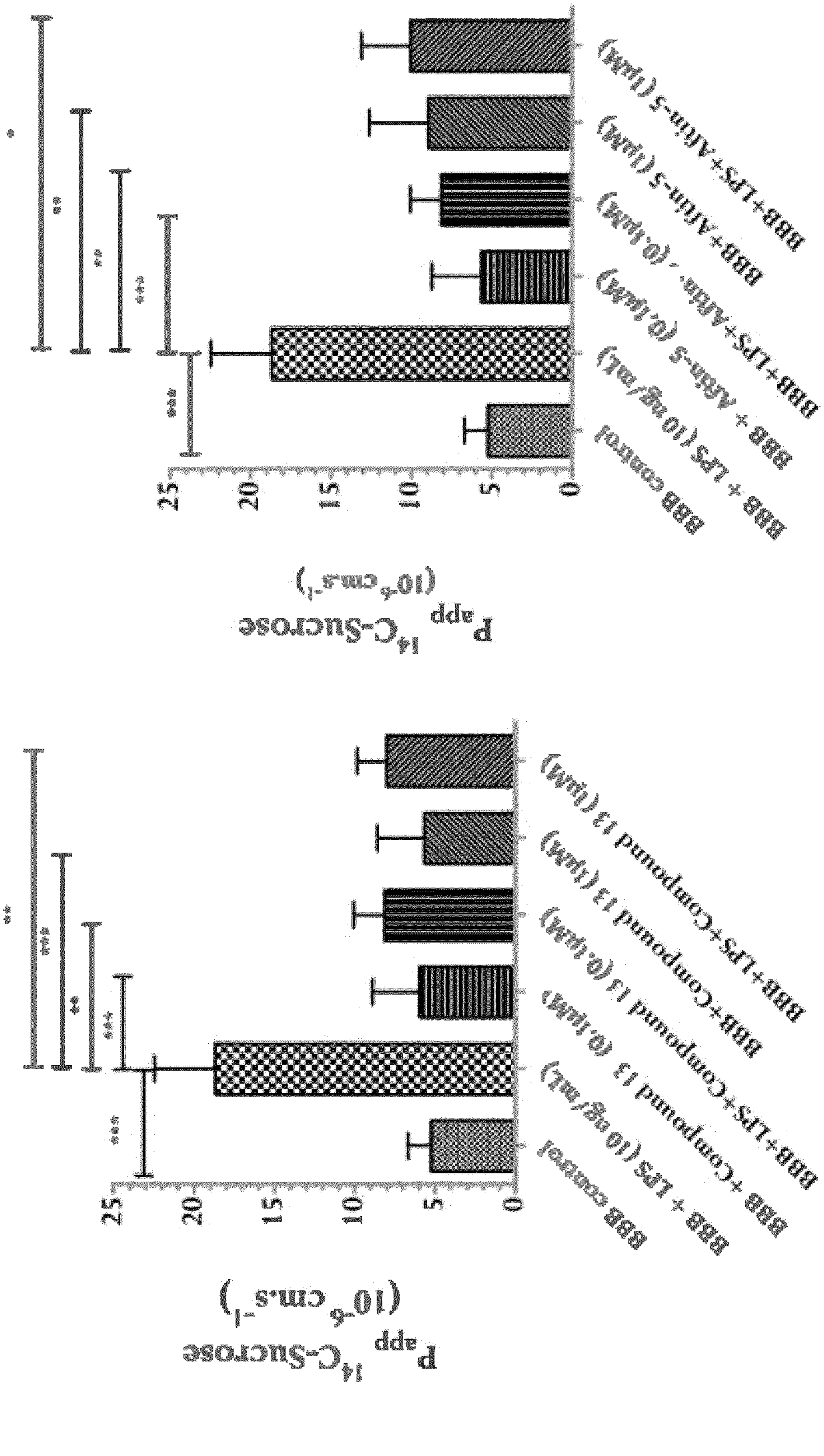

FIG. 2: Ability of Aftins to reverse in vitro BBB leakage under inflammatory stress FIG. 2A: The permeability of radiolabelled sucrose, a permeability marker, was studied on a primary rat cell-based BBB (blood-brain barrier) model after lipopolysaccharide (LPS) challenge.

First graph (left): y-axis: permeability of $^{14}C$-sucrose through the BBB ($10^{-6}$ cm·s$^{-1}$); x-axis (from left to right): BBB control (negative control); BBB+LPS (10 ng/mL) (positive control); BBB+Compound 13 (0.1 μM); BBB+LPS+Compound 13 (0.1 μM); BBB+Compound 13 (1 μM); BBB+LPS+Compound 13 (1 μM).

Second graph (right): y-axis: permeability of $^{14}C$-sucrose through the BBB ($10^{-6}$ cm·s$^{-1}$); x-axis (from left to right): BBB control (negative control); BBB+LPS (10 ng/mL) (positive control); BBB+Aftin-5 (0.1 μM); BBB+LPS+Aftin-5 (0.1 μM); BBB+Aftin-5 (1 μM); BBB+LPS+Aftin-5 (1 μM).

Figure 2B:
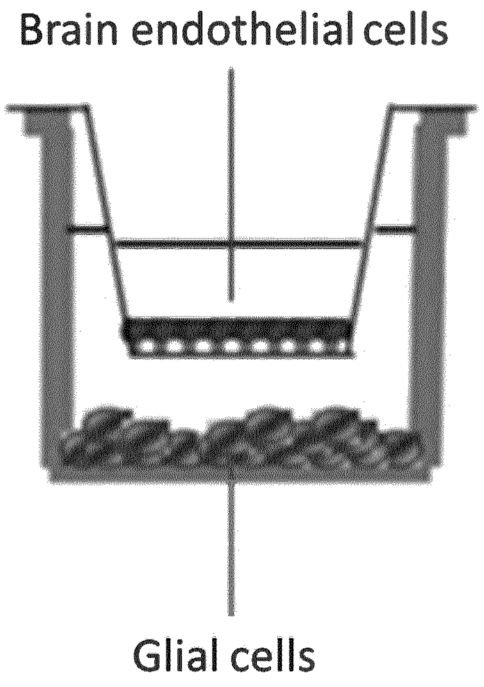

FIG. 2B: Schematic view of the primary rat cell-based BBB model after LPS challenge

DEFINITIONS

As used herein, the term "individual" refers to either an animal, such as a valuable animal for breeding, company or preservation purposes, or preferably a human or a human child, which is afflicted with, or has the potential to be afflicted with one or more diseases and conditions described herein.

In particular, as used in the present application, the term "individual" refers to a mammal such as a rodent, cat, dog, primate or human, preferably said subject is a human.

The identification of those individuals who are in need of treatment of herein-described diseases and conditions is well within the ability and knowledge of one skilled in the art. A veterinarian or a physician skilled in the art can readily identify, by the use of clinical tests, physical examination, medical/family history or biological and diagnostic tests, those individuals who are in need of such treatment.

As used herein the term "infant" refers to a human child, preferably under 2 years, in particular under 1 year, and more particularly under 8 months. Even more particularly an infant may be a "newborn" or "neonate" referring to an infant in the first 28 days after birth.

The term "treatment-effective amount" refers to a concentration of compound that is effective in treating the concerned diseases or which alone stimulates the desired outcome, i.e. alleviates or eradicates the symptoms of the encompassed disorder.

As used herein, the term "pharmaceutically acceptable" refers to those compounds, materials, excipients, compositions or dosage forms which are, within the scope of sound medical judgment, suitable for contact with the tissues of human beings and animals without excessive toxicity, irritation, allergic response or other problem complications commensurate with a reasonable benefit/risk ratio.

Within the scope of the invention, the term 'treatment' refers to a therapy intended to partially or totally alleviating at least one symptom linked to acquired brain injury (ABI) as much more defined herein after, and in particular of hypoxic injuries, and more particularly of neonatal hypoxia-ischemia (HI) and neonatal hypoxic-ischemic encephalopathy (HIE). In said circumstance, the individual may be from a specific cohort of individuals diagnosed for having an acquired brain injury (ABI), or presenting at least one symptom of an acquired brain injury (ABI) such as for example signs of abnormalities in BBB permeability as much more detailed herein after.

According to a preferred embodiment, the individual to be treated according to the invention is an individual suffering from a non-traumatic acquired brain injury (ABI), in particular hypoxic injuries, and more particularly from neonatal hypoxia-ischemia (HI) or neonatal hypoxic-ischemic encephalopathy (HIE). In a preferred embodiment, said individual is an infant. Preferably, said infant is a neonate.

DETAILED DESCRIPTION OF THE INVENTION

Surprisingly, the inventors demonstrated the action of the compounds of formula (I) in decreasing a brain injury lesion. The examples below illustrate, through in vivo and in vitro models said new biological action of the compounds of formula (I) as defined herein after. Namely, in the well-characterized Rice-Vannucci neonatal HI model, the inventors demonstrated consistent decrease of the brain injury lesion (FIG. 1) and increase of neurotrophic markers in the brain after administration of Aftin compounds. In addition, they showed that the compounds of formula (I) as defined herein after are able to reverse BBB leakage under inflammatory stress (FIG. 2).

Indeed, the inventors have surprisingly demonstrated that Aftin compounds of formula (I) are able to reduce infarct volumes in male and female neonatal rats exposed to HI, making the proof-of-concept that administration of the Aftin compound promotes regeneration of the neurological tissue so as to repair the damage induced by the brain lesions. The pharmacological effects are correlated with BBB integrity restoration.

According to a first aspect, a subject-matter of the present invention relates to a compound of formula (I), for use in the treatment of non-traumatic acquired brain injury (ABI), (I)

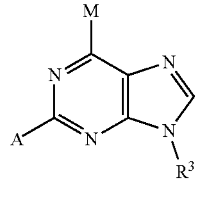

in which

M represents a $NR^1R^2$ group, an $OR^1$ group or a $SR^1$ group,

A represents a $NR^4R^5$ group, an $OR^{10}$ group or a hydrogen atom, $R^1$ is an aryl group, a heteroaryl group, a $-CH_2$-aryl group or a $-CH_2$-heteroaryl group, said aryl and heteroaryl being optionally substituted with one or more substituents independently chosen from a halogen atom, a $CF_3$ group, a hydroxyl group, an $OR^6$ group, a $SR^6$ group, a $NR^6R^7$ group, a CN group, a $CONR^6R^7$ group, a $SOR^6$ group, a $SO_2R^6$ group, an azido group ($—N_3$), an aryl group, a heteroaryl group and a ($C_1$-$C_6$)alkyl group, $R^2$ is a ($C_1$-$C_6$)alkyl group or a ($C_1$-$C_6$)cycloalkyl group said alkyl and cycloalkyl group being optionally substituted with one or more substituents independently chosen from a halogen atom, a hydroxyl group and a $NH_2$ group, or $R^1$ forms together with $R^2$ and with the nitrogen atom that bears $R^1$ and $R^2$ an heterobicyclic ring, $R^6$ and $R^7$ represent independently of each other a hydrogen atom or a ($C_1$-$C_6$)alkyl group, $R^3$ is a ($C_1$-$C_6$)alkyl group, a ($C_1$-$C_6$)cycloalkyl group, an aryl group, a $—CH_2$-aryl group, a $CH_2—$($C_1$-$C_6$)cycloalkyl group or a $—CH_2$-heteroaryl group, said alkyl, cycloalkyl, aryl and heteroaryl group being optionally substituted with one or more substituents independently chosen from a halogen atom, a hydroxyl group and a $NH_2$ group, $R^4$ is a hydrogen atom, a ($C_1$-$C_6$) alkyl group, a ($C_1$-$C_6$) cycloalkyl group, an aryl group or a heteroaryl group, said alkyl and cycloalkyl group being optionally substituted with one or more substituents independently chosen from a halogen atom, a hydroxyl group and a $NH_2$ group, said aryl and heteroaryl being optionally substituted with one or more substituents chosen from a halogen atom, a hydroxyl group, a $NH_2$ group and a $NH—R^9$ group, $R^9$ is a heteroaryl group optionally substituted with one or more substituents chosen from a halogen atom, a hydroxyl group, a $NH_2$ group and a heteroaryl group, $R^5$ is a hydrogen atom, a ($C_1$-$C_8$)alkyl group or a ($C_1$-$C_6$)cycloalkyl group, said alkyl and cycloalkyl group being optionally substituted with one or more substituents independently chosen from a halogen atom, a hydroxyl group, an azido group, a $—OCOR^a$ group and a $NR^6R^7$ group, one or more of the carbon atoms of said alkyl or cycloalkyl group being optionally replaced by a nitrogen atom, $R^a$ represents a ($C_1$-$C_6$)alkyl group, said alkyl group being optionally substituted by an amino group, or alternatively $R_4$ and $R_5$ may form with the nitrogen atom bearing them a ($C_3$-$C_6$)heterocylcoalkyl group, said ($C_3$-$C_6$) heterocylcoalkyl group being optionally substituted by one or more substituents independently chosen from a ($C_1$-$C_4$)alkyl group, a $NR^6R^7$ group and a halogen atom, $R^{10}$ is a hydrogen atom, a ($C_1$-$C_6$)alkyl group, a ($C_1$-$C_6$) cycloalkyl group, an aryl group, a heteroaryl group, a $—CH_2$-aryl group or $—CH_2$-heteroaryl group, said aryl being optionally substituted with one or more substituents chosen from a halogen atom, a hydroxyl group, an $OR^6$ group, a $SR^6$ group, a $NR^6R^7$ group, a CN group, a $CONR^6R^7$ group, a $SO_2NR^6R^7$ group, a $SOR^6$ group, a $SO_2R^6$ group and an azido group ($N_3$), and its addition salts with pharmaceutically acceptable acids.

In the context of the present invention, the term "halogen" is understood to mean chlorine (Cl), fluorine (F), bromine (Br) or iodine (I).

The term "alkyl" as used herein refers to a linear or branched, saturated aliphatic hydrocarbon group. For instance, a ($C_1$-$C_6$) alkyl group denotes a linear or branched carbon chain of 1 to 6 carbon atoms. Examples are, but are not limited to, methyl, ethyl, propyl, isopropyl, butyl, isobutyl, methylbutyl.

The term "cycloalkyl" refers to a cyclic alkyl group that may be substituted by one or more ($C_1$-$C_6$)alkyl groups. Examples are, but are not limited to cyclopropyl, cyclobutyl, cyclopentyl, methylcyclopropyl, methylcyclobutyl.

The term "($C_3$-$C_6$)heterocycloalkyl" refers to a ($C_3$-$C_6$) cycloalkyl group wherein one or two of the carbon atoms are replaced with a heteroatom such as oxygen or nitrogen. Examples are, but not limited to, morpholinyl, piperidinyl, pyrrolidinyl, piperazinyl and homopiperazinyl.

The term "aryl" refers to a monocyclic or polycyclic aromatic hydrocarbon radical of 6-20 atoms derived by the removal of one hydrogen from a carbon atom of a parent aromatic ring system. Typical aryl groups include, but are not limited to 1 ring or 2 or 3 rings fused together. Said radical is typically derived from the rings selected from benzene, naphthalene, anthracene, and the like. "Aryl" preferably refers to radicals such as phenyl.

The term "heteroaryl" denotes a 5- or 6-membered aromatic ring comprising 1 or 2 heteroatoms or a bi-cyclic or tricyclic aromatic nucleus comprising from 1 to 4 heteroatoms, and at least one of the rings of which has 6 ring members, the other fused ring or rings having 5 or 6 ring members. Examples are, but not limited to, pyridyl, pyrrolyl, thiophenyl, thiazolyl, triazolyl, isothiazolyl, isoxazolyl, imidazolyl, pyrazolyl, pyrazinyl, pyrimidinyl and pyridazinyl.

The term "heteroatom" is understood to mean nitrogen (N), oxygen (O) or sulphur (S).

Preferably, the heteroaryl comprises at least one nitrogen atom. In particular, the heteroaryl does not comprise an oxygen atom. Finally, very preferably, the heteroaryl comprises only nitrogen as heteroatom(s). Thus, advantageously, the heteroaryl comprises from 1 to 4 nitrogen atoms.

Mention may more particularly be made of pyridyl, pyrrolyl, thiazolyl, pyrazolyl and triazolyl and even more particularly of pyridyl and pyrrolyl.

In the context of the present invention, the terms "aromatic ring", "aryl", and "heteroaryl" include all the positional isomers.

The term "heterobicyclic ring" refers to 8 to 14-membered bicyclic radical that comprises at least one heteroatom. Preferably one ring from the heterobicyclic ring is aromatic. In particular the heterobicyclic ring comprises only nitrogen as heteroatom(s). Finally, very particularly the heterobicyclic ring may be chosen from these 2 following radicals:

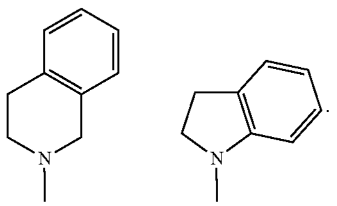

The M radical, when being $NR^1R^2$, may in particular be chosen among the following radicals (1) to (89):

(1)

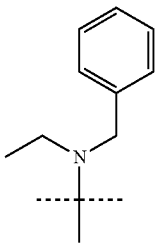

-continued
(2)
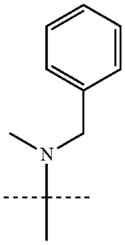
(3)
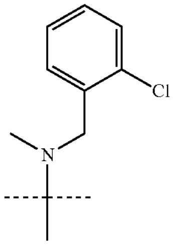
(4)
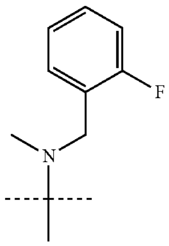
(5)
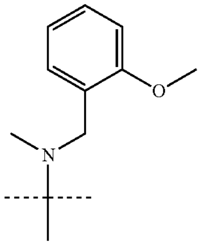
(6)
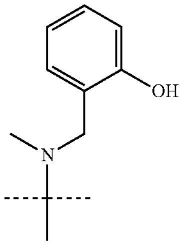
(7)
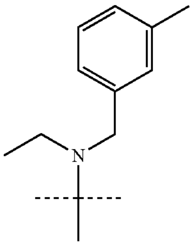
-continued
(8)
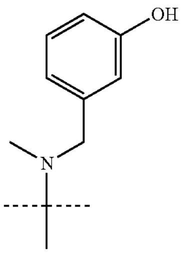
(9)
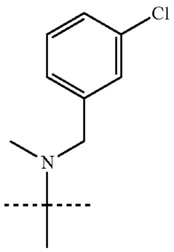
(10)
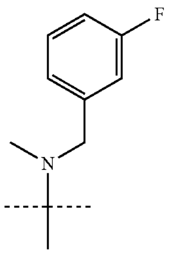
(11)
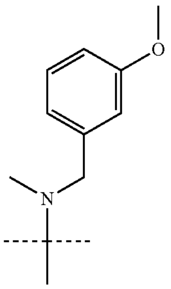
(12)
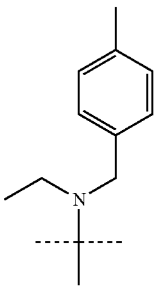

-continued
(13)
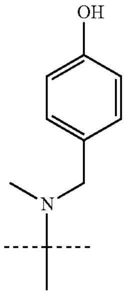
(14)
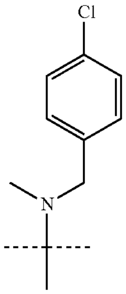
(15)
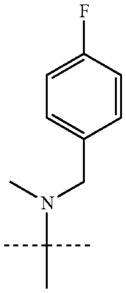
(16)
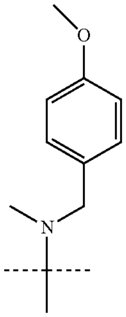
(17)
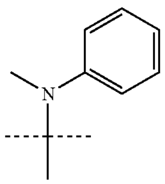
(18)
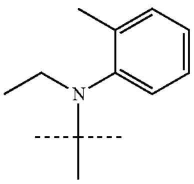
-continued
(19)
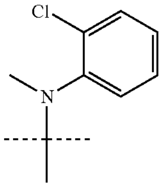
(20)
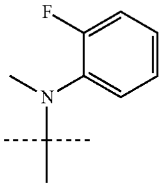
(21)
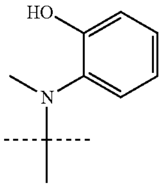
(22)
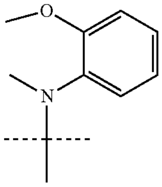
(23)
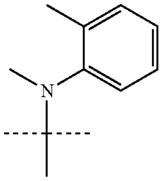
(24)
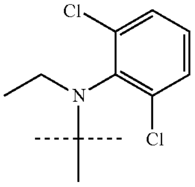
(25)
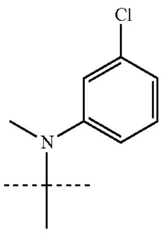

-continued
(26)
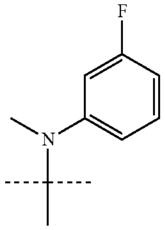
(27)
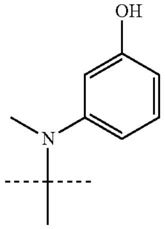
(28)
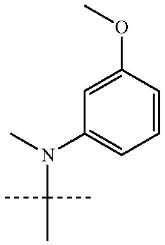
(29)
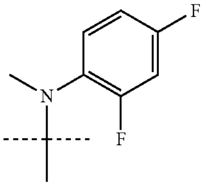
(30)
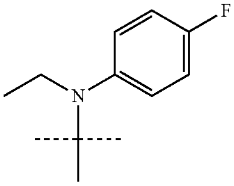
(31)
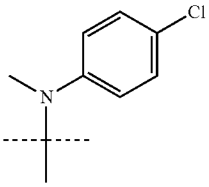
(32)
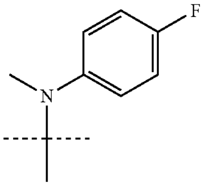
-continued
(33)
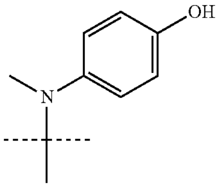
(34)
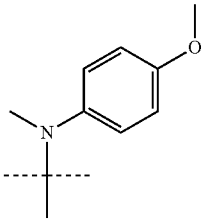
(35)
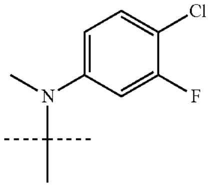
(36)
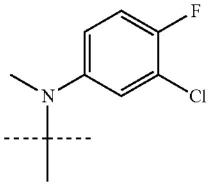
(37)
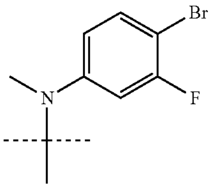
(38)
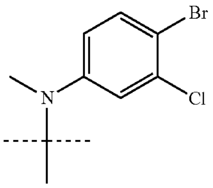
(39)
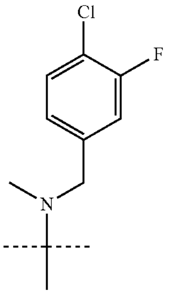

-continued
(40)
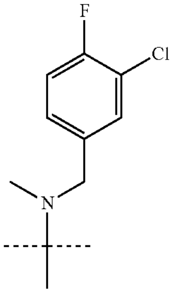
(41)
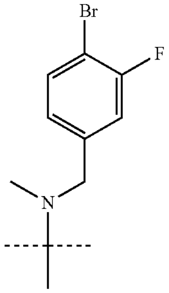
(42)
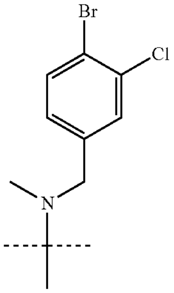
(43)
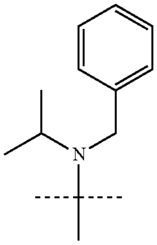
(44)
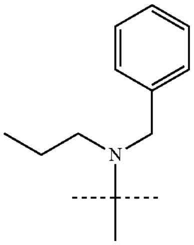
(45)
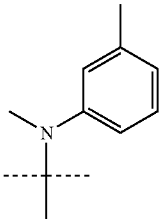
-continued
(46)
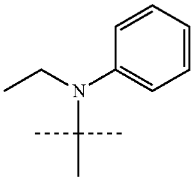
(47)
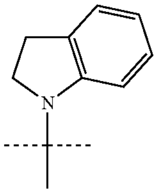
(48)
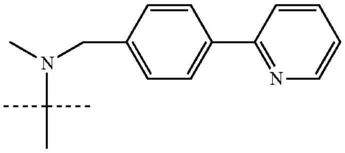
(49)
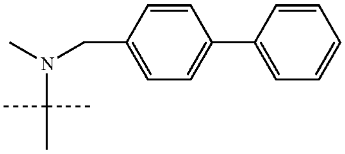
(50)
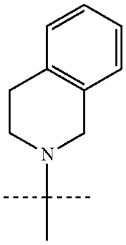
(51)
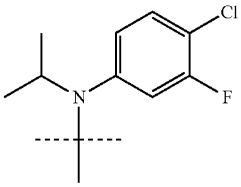
(52)
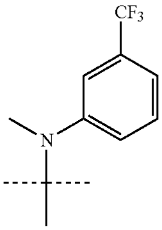

-continued
(53)
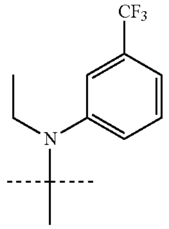
(54)
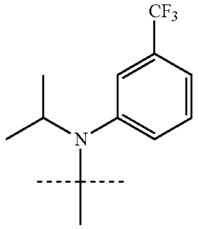
(55)
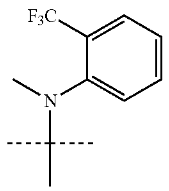
(56)
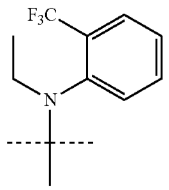
(57)
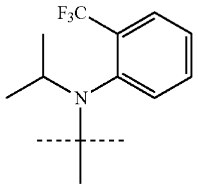
(58)
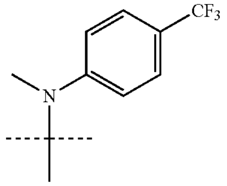
(59)
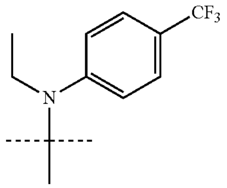
-continued
(60)
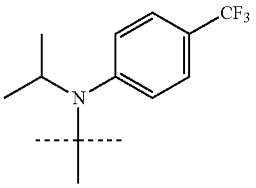
(61)
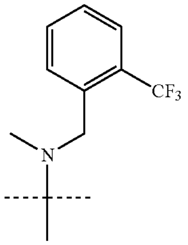
(62)
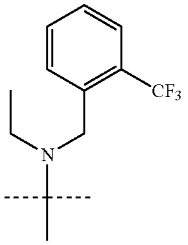
(63)
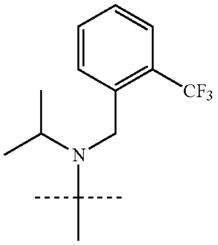
(64)
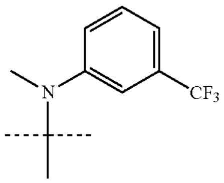
(65)
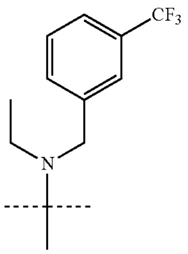

-continued
(66)
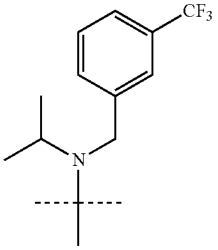
(67)
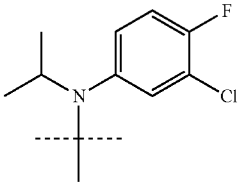
(68)
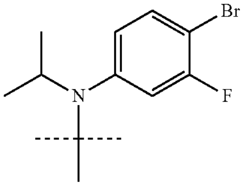
(69)
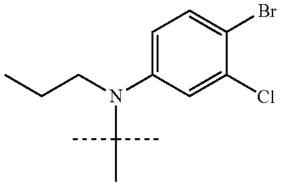
(70)
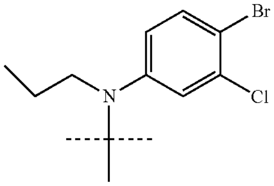
(71)
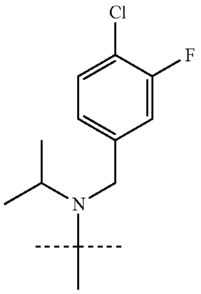
(72)
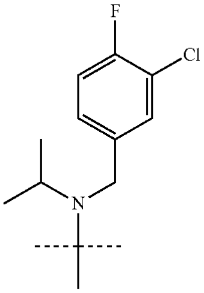
-continued
(73)
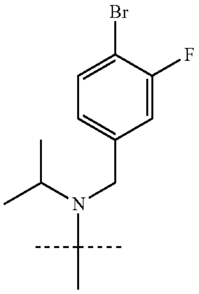
(74)
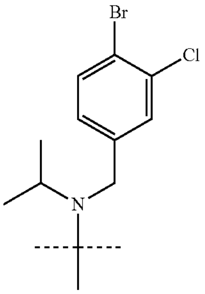
(75)
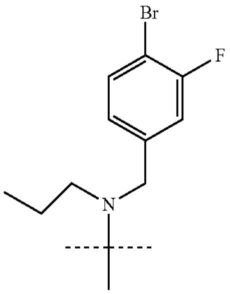
(76)
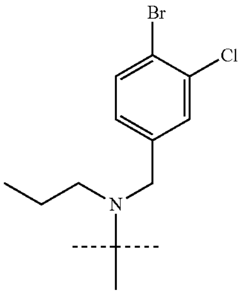
(77)
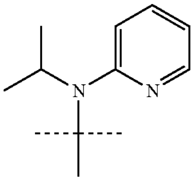
(78)
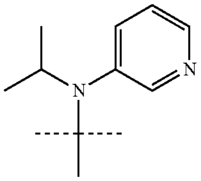

-continued
(79)
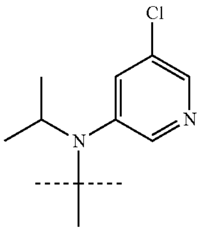
(80)
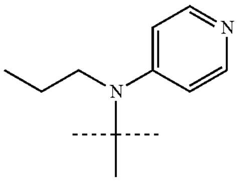
(81)
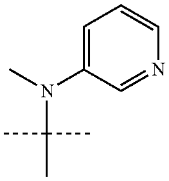
(82)
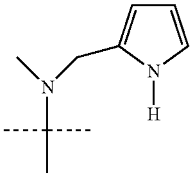
(83)
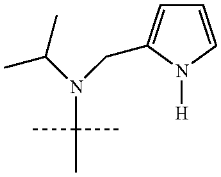
(84)
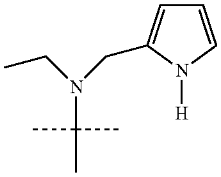
(85)
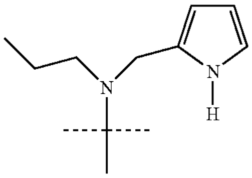
(86)
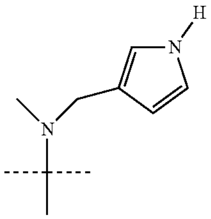
-continued
(87)
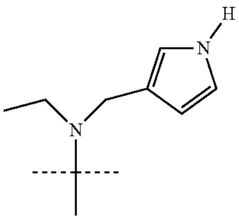
(88)
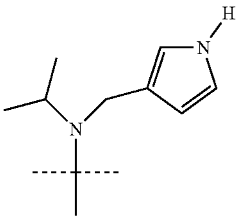
(89)
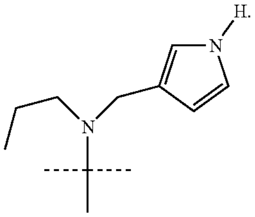
The A radical, when being $NR^4R^5$ may in particular be chosen among the following radicals (1') to (19'):
(1')
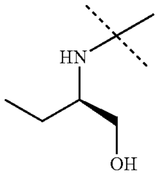
(2')
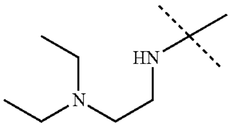
(3')
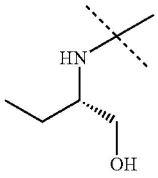
(4')
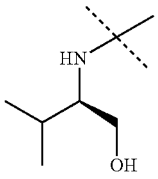

-continued
(5′)
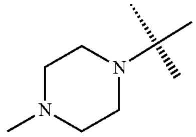
(6′)
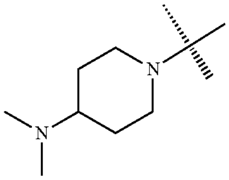
(7′)
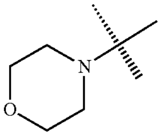
(8′)
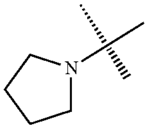
(9′)
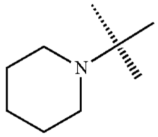
(10′)
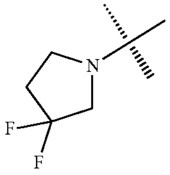
(11′)
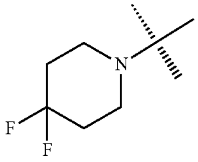
(12′)
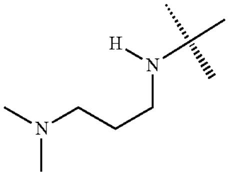
(13′)
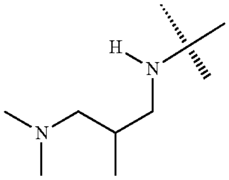
-continued
(14′)
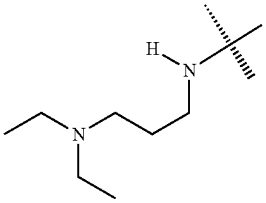
(15′)
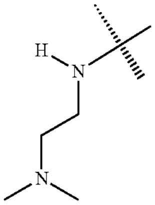
(16′)
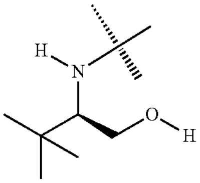
(17′)
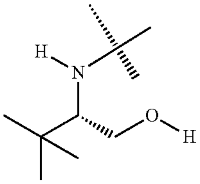
(18′)
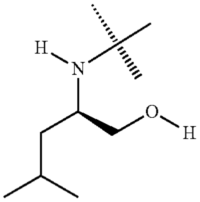
(19′)
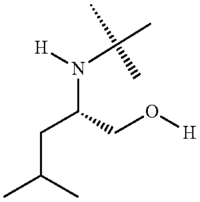
(20′)
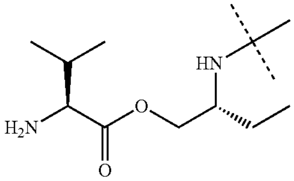

-continued (21')

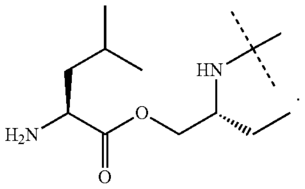

$R^3$ may in particular be chosen among the following radicals (1") to (14"):

(1")

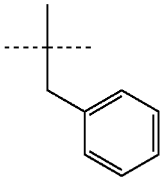

(2")

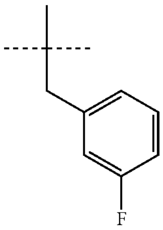

(3")

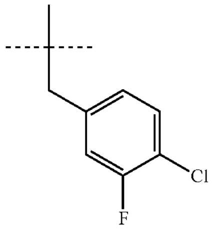

(4")

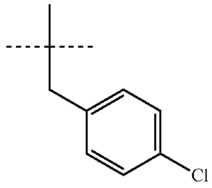

(5")

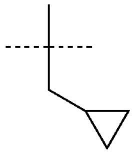

(6")

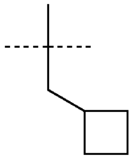

-continued (7")

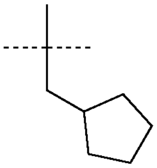

(8")

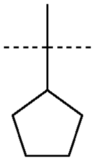

(9")

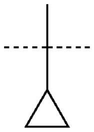

(10")

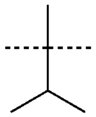

(11")

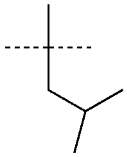

(12")

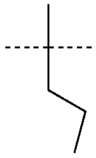

(13")

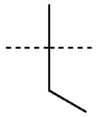

(14")

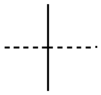

Among the compounds of general formula (I) for use according to the present invention, a first subgroup of compounds is formed from compounds for which M represents a $NR^1R^2$ group, an $OR^1$ group or a $SR^1$ group, $R^1$ is an aryl group, a $—CH_2$-aryl group, a heteroaryl or a $CH_2$-heteroaryl group, said aryl and heteroaryl being optionally substituted with one or more substituents independently chosen from a halogen atom, a $CF_3$ group, a hydroxyl group, an $OR^6$ group, a $CONR^6R^7$ group, an azido group ($—N_3$), an aryl group, a heteroaryl group and a ($C_1$-$C_6$)alkyl group, $R^2$ is a $(C_1-C_6)$alkyl group, or $R^1$ forms together with $R^2$ and with the nitrogen atom that bears $R^1$ and $R^2$ an heterobicyclic ring, $R^6$ and $R^7$ represent independently of each other a hydrogen atom or a $(C_1-C_6)$alkyl group.

Among the compounds of general formula (I) for use according to the present invention, a second subgroup of compounds is formed from compounds for which M represents a $NR^1R^2$ group, an $OR^1$ group or a $SR^1$ group;

$R^1$ is an aryl group, a —$CH_2$-aryl group, a heteroaryl or a $CH_2$-heteroaryl, said aryl being optionally substituted with one or more substituents chosen from a halogen atom, a $CF_3$ group, an $OR^6$ group, a $CONR^6R^7$ group, an aryl group, a heteroaryl group and a $(C_1-C_6)$alkyl group, $R^2$ is a $(C_1-C_6)$alkyl group, or $R^1$ forms together with $R^2$ and with the nitrogen atom that bears $R^1$ and $R^2$ an heterobicyclic ring, $R^6$ and $R^7$ represent independently of each other a hydrogen atom or a $(C_1-C_6)$alkyl group.

Among the compounds of general formula (I) for use according to the present invention, a third subgroup of compounds is formed from compounds for which M represents a $NR^1R^2$ group, an $OR^1$ group or a $SR^1$ group;

$R^1$ is a phenyl group, a benzyl group, a pyridine group, a —$CH_2$-pyridine group, a pyrrole group or a —$CH_2$-pyrrole group, said groups being optionally substituted with one substituent chosen from a fluorine atom, a chlorine atom, a $CF_3$ group, an $OR^6$ group, a $CONR^6R^7$ group, a phenyl group, a pyridinyl group and a methyl group, $R^2$ is a methyl group, an ethyl group, a n-propyl group or an isopropyl group, or $R^1$ forms together with $R^2$ and with the nitrogen atom that bears $R^1$ and $R^2$ an heterobicyclic ring chosen from these 2 following radicals:

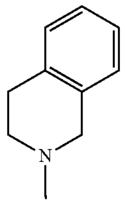

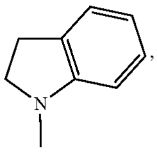, $R^6$ and $R^7$ represent independently of each other a hydrogen atom or a methyl group.

Among the compounds of general formula (I) for use according to the present invention, a fourth subgroup of compounds is formed from compounds for which A represents a $NR^4R^5$ group, an $OR^{10}$ group or a hydrogen atom;

$R^4$ is a hydrogen atom or a $(C_1-C_6)$alkyl group, said alkyl group being optionally substituted with one hydroxyl group, $R^5$ is a hydrogen atom, a $(C_1-C_8)$alkyl group or a $(C_1-C_6)$cycloalkyl group, said alkyl group being optionally substituted with one or two hydroxyl group or a —$OCOR^a$ group, one of the carbon atoms of said alkyl or cycloalkyl group being optionally replaced by a nitrogen atom, $R^a$ represents a $(C_1-C_6)$alkyl group, said alkyl group being optionally substituted by an amino group, or alternatively $R^4$ and $R^5$ may form with the nitrogen atom bearing them a $(C_3-C_6)$heterocylcoalkyl group, said $(C_3-C_6)$heterocylcoalkyl group being optionally substituted by one or more substituents independently chosen from a $(C_1-C_4)$alkyl group, a $NR^6R^7$ group and a halogen atom, $R^{10}$ is a —$CH_2$-aryl group.

Among the compounds of general formula (I) for use according to the present invention, a fifth subgroup of compounds is formed from compounds for which A represents a $NR^4R^5$ group, an $OR^{10}$ group or a hydrogen atom;

$R^4$ is a hydrogen atom or a 2-hydroxyethyl group,

R5 is a hydrogen atom, a 1-hydroxybutan-2-yl group, a 1-hydroxy-3-methylbutan-2-yl group, a 1,2-dihydroxypropan-3-yl group, a N-ditehylaminoeth-2-yl group, a piperidin-4-yl group, a 2-hydroxyethyl group, or anyone of the radicals (12') to (21') as defined above, or alternatively $R^4$ and $R^5$ may form with the nitrogen atom bearing them a morpholinyl group, a piperazinyl group, a pyrrolidinyl group, a piperidinyl group, said groups being optionally substituted by one or more substituents independently chosen from a $(C_1-C_4)$alkyl group, a $NR^6R^7$ group and a halogen atom, and for example from anyone of the radicals (5') to (11') as defined above, $R^6$ and $R^7$ represent independently of each other a hydrogen atom or a methyl group, $R^{10}$ is a benzyl group.

Among the compounds of general formula (I) for use according to the present invention, a sixth subgroup of compounds is formed from compounds for which $R^3$ represents a $(C_1-C_6)$alkyl group, a $(C_1-C_6)$cycloalkyl group or a —$CH_2$-aryl group, said aryl being optionally substituted by one or more substituents independently chosen from halogen atoms.

Among the compounds of general formula (I) for use according to the present invention, a seventh subgroup of compounds is formed from compounds for which $R^3$ represents anyone of the radicals (1") to (14") as defined above, and more particularly a cyclopentyl group, an isopropyl group or a benzyl group.

Among the compounds of general formula (I) for use according to the present invention, an eighth subgroup of compounds is formed by the compounds of general formula (I) in which, simultaneously, A and/or M and/or $R^3$ are as defined in the above subgroups.

Among the compounds of general formula (I) for use according to the present invention, a ninth subgroup of compounds is formed by the compounds of general formula (I) in which, M represents a $NR^1R^2$ group, $R^2$ represents a $(C_2-C_6)$alkyl group or a $(C_1-C_6)$cycloalkyl group said alkyl and cycloalkyl group being optionally substituted with one or more substituents chosen from a halogen atom, a hydroxyl group and a $NH_2$ group, and $R^1$, A and $R^3$ are as defined above, with $R^3$ being preferably an isopropyl group, a benzyl group or a cyclopentyl group.

According to said particular embodiment, M is preferably a radical (1), (2), (15), (17), (25), (43) or (44) as defined herein above and even more preferably a radical (1), (43) or (44) as defined herein above.

Compounds 13, 15, 18, 20, 22 and 23 as defined herein after in Table 1, and their pharmaceutically acceptable salts are in particular encompassed within the scope of said particular embodiment.

Among the compounds of general formula (I) for use according to the present invention, a tenth subgroup of compounds is formed by the compounds of general formula (I) in which, M represents a $NR^1R^2$ group, $R^3$ is a $(C_1-C_6)$cycloalkyl group, an aryl group, a —$CH_2$-aryl group or a —$CH_2$-heteroaryl group, said cycloalkyl, aryl and heteroaryl group being optionally substituted with one or more substituents chosen from a halogen atom, a hydroxyl group and a $NH_2$ group, $R^3$ being preferably a benzyl group or a cyclopentyl group, $R^1$, A and $R^2$ are as defined above.

According to said particular embodiment, M is preferably a radical (1), (2), (15), (17), (25), (43) or (44) as defined herein above, and even more preferably a radical (1) or (2).

Compounds 14, 15, 18 and 22 as defined herein after in Table 1, and their pharmaceutically acceptable salts are in particular encompassed within the scope of said particular embodiment.

Among the compounds of general formula (I) for use according to the present invention, an eleventh subgroup of compounds is formed by the compounds M represents a $NR^1R^2$ group, an $OR^1$ group or a $SR^1$ group, A represents a group a $NR^4R^5$ group selected from the radicals (1'), (2'), (3') and (4'), and $R^1$, $R^2$ and $R^3$ are as defined above, with $R^3$ being preferably an isopropyl group, a benzyl group or a cyclopentyl group.

According to said particular embodiment, $R^1$ is an aryl group, a heteroaryl group, a —$CH_2$-aryl group or a —$CH_2$-heteroaryl group, said aryl and heteroaryl being optionally substituted with one substituent chosen from a halogen atom, a $CF_3$ group, a hydroxyl group, an $OR^6$ group, a $SR^6$ group, a $NR^6R^7$ group, a CN group, a $CONR^6R^7$ group, a $SOR^6$ group, a $SO_2R^6$ group, an azido group (—$N_3$) and a ($C_1$-$C_6$)alkyl group.

According to said particular embodiment, M is preferably a radical (1), (2), (15), (17), (25), (43) or (44) as defined herein above and even more preferably a radical (1), (2) or (17).

Compounds 13, 14, 15, 18, 20, 22, 23, 26, 38 and Aftin-5, as defined herein after in Table 1, and their pharmaceutically acceptable salts, are in particular encompassed within the scope of said particular embodiment.

Subfamilies of compounds of formula (I) are also reported herein after, still conform to EP 2 664 619, which may also be used as medicament. Therefore, said compounds of formula (Ia), (Ib), (Ic), (Id), (Ie) useful as medicament are a further subject-matters forming part of the present invention.

Compound of Formula (Ia)

They are defined as follows:

(Ia)

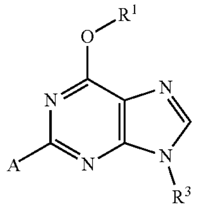

in which

A represents a $NR^4R^5$ group or an $OR^{10}$ group, $R^1$, $R^5$ and $R^{10}$are as defined above, $R^3$ is a ($C_1$-$C_6$)alkyl group, a ($C_1$-$C_6$)cycloalkyl group, an aryl group, a —$CH_2$-aryl group or a —$CH_2$-heteroaryl group, said alkyl, cycloalkyl, aryl and heteroaryl group being optionally substituted with one or more substituents chosen from a halogen atom, a hydroxyl group and a $NH_2$ group, $R^4$ is a hydrogen atom, a ($C_1$-$C_6$) alkyl group or a ($C_1$-$C_6$) cycloalkyl group, said alkyl and cycloalkyl group being optionally substituted with one or more substituents chosen from a halogen atom, a hydroxyl group and a $NH_2$ group.

According to a particular embodiment, the present invention relates to a compound of formula (Ia), as defined above, for use according to the present invention, in which, A represents a $NR^4R^5$ group or an $OR^{10}$ group, $R^1$ is a —$CH_2$-aryl group, preferably a benzyl group, $R^3$ is a ($C_1$-$C_6$)alkyl group or a ($C_1$-$C_6$)cycloalkyl group, preferably a methyl, ethyl, cyclopropyl, cyclobutyl, methylcyclopropyl, methylcyclobutyl or isopropyl group, in particular an isopropyl group, $R^4$ is a hydrogen atom, $R^5$ is a ($C_1$-$C_6$)alkyl group or a ($C_1$-$C_6$)cycloalkyl group, said alkyl and cycloalkyl group being optionally substituted with one hydroxyl group, preferably $R^5$ is a methyl, ethyl, cyclopropyl, cyclobutyl, methylcyclopropyl, methylcyclobutyl or 1-hydroxybutan-2-yl group in particular a 1-hydroxybutan-2-yl group, $R^{10}$ is a —$CH_2$-aryl group, preferably a benzyl group, and its addition salts with pharmaceutically acceptable acids.

Aftin-3, as represented herein after, is encompassed within the scope of said formula (Ia).

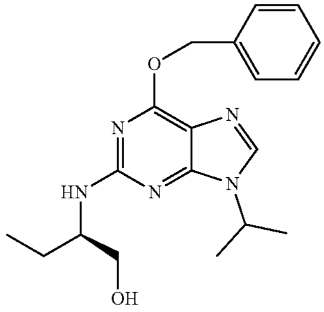 [SMILES: CC[C@H](CO)Nc1nc(OCc2ccccc2)c2ncn(C(C)C)c2n1]

The compounds Aftin-3 is disclosed in Tang et al. (J. Biol. Chem. 2005; 280, 31220-21229) as a negative control in a kinase activity test.

Compounds 31, 32 and 46 as defined herein after in Table 1, and their pharmaceutically acceptable salts, are in particular encompassed within the scope of formula (Ia).

Compound of Formula (Ib)

They are defined as follows:

(Ib)

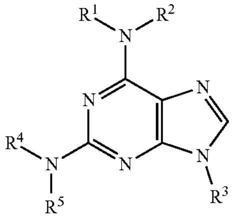

in which $R^1$, $R^2$ and $R^5$ are as defined above, $R^3$ is a ($C_1$-$C_6$)alkyl group, a ($C_1$-$C_6$)cycloalkyl group, an aryl group, a —$CH_2$-aryl group or a —$CH_2$-heteroaryl group, said alkyl, cycloalkyl, aryl and heteroaryl group being optionally substituted with one or more substituents chosen from a halogen atom, a hydroxyl group and a $NH_2$ group, $R^4$ is a hydrogen atom, a ($C_1$-$C_6$) alkyl group or a ($C_1$-$C_6$) cycloalkyl group, said alkyl and cycloalkyl group being optionally substituted with one or more substituents chosen from a halogen atom, a hydroxyl group and a $NH_2$ group, and its addition salts with pharmaceutically acceptable acids.

Compounds 13, 14, 15, 18, 20, 22, 23, 26 and 38 as defined herein after in Table 1, and their pharmaceutically acceptable salts, are in particular encompassed within the scope of formula (Ib).

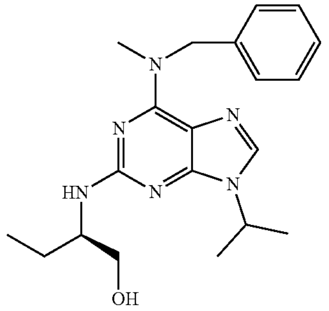 [SMILES: CC[C@H](CO)Nc1nc(N(C)Cc2ccccc2)c2ncn(C(C)C)c2n1]

Aftin-4 is encompassed within the scope of said formula (Ib). The compounds Aftin-4 is disclosed in Tang et al. (J. Biol. Chem. 2005; 280, 31220-21229) as a negative controls in a kinase activity test.

Aftin-5, as represented herein after, is also encompassed within the scope of said formula (Ib).

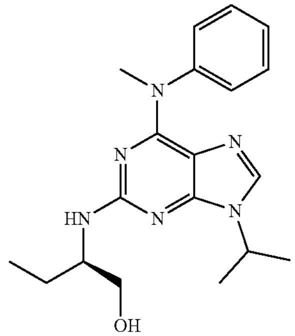 [SMILES: CC[C@H](CO)Nc1nc(N(C)c2ccccc2)c2ncn(C(C)C)c2n1]

Aftin-5 is disclosed and covered in EP 2 664 619.

According to a particular embodiment, the present invention relates to a compound of formula (Ib), as defined above, for use according to the present invention, in which, the $NR^1R^2$ radicals are chosen from the radicals (1) to (89) as defined above.

According to an even more particular embodiment, the present invention relates to a compound of formula (Ib), as defined above, for use according to the present invention, in which, the $NR^1R^2$ radical is as defined above, preferably, $NR^1R^2$ radical is chosen from radicals of formulae (1), (2), (11), (15), (17), (25), (32), (34) and (43) to (51) as defined above, and more particularly chosen from radicals of formulae (1), (2), (15), (17), (25), (43) and (44), and even more particularly chosen from radicals of formulae (1), (2) and (17).

$R^3$ is a ($C_1$-$C_6$) alkyl group, a ($C_1$-$C_6$) cycloalkyl group or a —$CH_2$-aryl group, a $CH_2$-($C_1$-$C_6$) cylcoalkyl group, preferably $R^3$ is a methyl, ethyl, cyclopropyl, cyclobutyl, methylcyclopropyl, methylcyclobutyl, isopropyl, cyclopentyl or benzyl group, in particular $R^3$ is an isopropyl, cyclopentyl or benzyl group, $R^4$ is a hydrogen atom, a ($C_1$-$C_6$) alkyl group or a ($C_1$-$C_6$)cycloalkyl group, said alkyl and cycloalkyl group being optionally substituted with one or more hydroxyl group, preferably $R^4$ is a methyl, ethyl, cyclopropyl, cyclobutyl, methylcyclopropyl, methylcyclobutyl or 2-hydroxyethyl group or a hydrogen atom, in particular $R^4$ is a 2-hydroxyethyl group or a hydrogen atom, $R^5$ is a hydrogen atom, a ($C_1$-$C_6$) alkyl group or a ($C_1$-$C_6$) cycloalkyl group, said alkyl and cycloalkyl group being optionally substituted with one or more hydroxyl group or a —OCOR$^a$ group, one or more of the carbon atoms of said alkyl and cycloalkyl group being optionally replaced by a nitrogen atom, with R$^a$ represents a ($C_1$-$C_6$)alkyl group, said alkyl group being optionally substituted by an amino group.

Preferably $R^5$ is a methyl, ethyl, cyclopropyl, cyclobutyl, methylcyclopropyl, methylcyclobutyl, 1-hydroxybutan-2-yl, 1-hydroxy-3-methylbutan-2-yl, 1,2-dihydroxypropan-3-yl, N-diethylaminoeth-2-yl, piperidin-4-yl or 2-hydroxyethyl group, or a hydrogen atom or a L-valyl ester of [(2R)-2-butyl], in particular $R^5$ is a 1-hydroxybutan-2-yl, 1-hydroxy-3-methylbutan-2-yl, 1,2-dihydroxypropan-3-yl, N-diethylaminoeth-2-yl, piperidin-4-yl or 2-hydroxyethyl group or a hydrogen atom, and its addition salts with pharmaceutically acceptable acids.

Compound of Formula (Ic)

They are defined as follows:

(Ic)

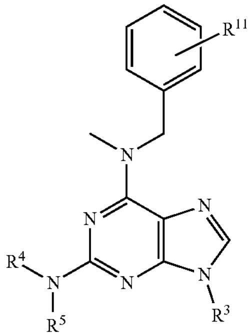

in which, $R^3$ is a ($C_1$-$C_6$) alkyl group, a ($C_1$-$C_6$) cycloalkyl group, a —$CH_2$-aryl group or a —$CH_2$-heteroaryl group, preferably $R^3$ is a methyl, ethyl, cyclopropyl, cyclobutyl, methylcyclopropyl, methylcyclobutyl, isopropyl, cyclopentyl or benzyl group, in particular $R^3$ is an isopropyl, cyclopentyl or benzyl group, $R^4$ is a hydrogen atom, $R^5$ is a hydrogen atom, a ($C_1$-$C_6$) alkyl group or a ($C_1$-$C_6$)cycloalkyl group, said alkyl and cycloalkyl group being optionally substituted with one or more hydroxyl group, a —OCOR$^a$ group, one or more of the carbon atoms of said cycloalkyl being optionally substituted by a nitrogen atom, preferably $R^5$ is a methyl, ethyl, cyclopropyl, cyclobutyl, methylcyclopropyl, methylcyclobutyl, 1-hydroxybutan-2-yl, 1,2-dihydroxypropan-3-yl or piperidin-4-yl group, a L-valyl ester of [(2R)-2-butyl] or a hydrogen atom, in particular $R^5$ is a 1-hydroxybutan-2-yl, 1,2-dihydroxypropan-3-yl, or piperidin-4-yl group, or a hydrogen atom, R$^a$ represents a ($C_1$-$C_6$)alkyl group, said alkyl group being optionally substituted by an amino group, $R^{11}$ is chosen from a halogen or a hydrogen atom, an $OR^6$ group, a $CONR^6R^7$ group, an aryl group and a heteroaryl group, preferably $R^{11}$ is an $OR^6$, $CONR^6R^7$, pyridinyl, phenyl group, or a fluorine or a hydrogen atom, $R^6$ and $R^7$ represent independently of each other a hydrogen atom or a $(C_1-C_6)$alkyl group, and its addition salts with pharmaceutically acceptable acids.

Compounds 14, and 38 as defined herein after in Table 1, and their pharmaceutically acceptable salts, are in particular encompassed within the scope of formula (Ic).

Compound of Formula (Id)

They are defined as follows:

(Id)

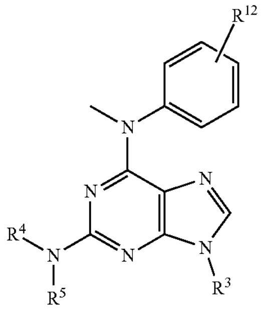

in which, $R^3$ is a $(C_1-C_6)$ alkyl group, a $CH_2$-aryl group, a —$CH_2$-heteroaryl group or a $(C_1-C_6)$cycloalkyl group, preferably $R^3$ is a methyl, ethyl, cyclopropyl, cyclobutyl, methylcyclopropyl, methylcyclobutyl, isopropyl or cyclopentyl group, in particular $R^3$ is an isopropyl or cyclopentyl group, $R^4$ is a hydrogen atom, a $(C_1-C_6)$ alkyl group or a $(C_1-C_6)$ cycloalkyl group, said alkyl and cycloalkyl group being optionally substituted with one or more hydroxyl group, preferably $R^4$ is a methyl, ethyl, cyclopropyl, cyclobutyl, methylcyclopropyl, methylcyclobutyl or 2-hydroxyethyl group or a hydrogen atom, in particular $R^4$ is a 2-hydroxyethyl group or a hydrogen atom, $R^5$ is a $(C_1-C_6)$alkyl group or a $(C_1-C_6)$ cycloalkyl group, said alkyl and cycloalkyl group being optionally substituted with one or more hydroxyl group or a —$OCOR^a$ group, preferably $R^5$ is a methyl, ethyl, cyclopropyl, cyclobutyl, methylcyclopropyl, methylcyclobutyl, a L-valyl ester of [(2R)-2-butyl], 1-hydroxybutan-2-yl or 2-hydroxyethyl group, in particular $R^5$ is a 1-hydroxybutan-2-yl or 2-hydroxyethyl group, $R^a$ represents a $(C_1-C_6)$alkyl group, said alkyl group being optionally substituted by an amino group, $R^{12}$ is chosen from a halogen, a $CF_3$ group or a hydrogen atom, an $OR^6$ group and a $(C_1-C_6)$alkyl group, preferably $R^{12}$ is a hydrogen, a $CF_3$ group, fluorine or chloride atom, or an $OR^6$ or methyl group, $R^6$ is a $(C_1-C_6)$ alkyl group, preferably, $R^6$ is a methyl group, and its addition salts with pharmaceutically acceptable acids.

Compounds 26 and Aftin-5 as defined herein after in Table 1, and their pharmaceutically acceptable salts, are in particular encompassed within the scope of formula (Id).

Compound of Formula (Ie)

They are defined as follows:

(Ie)

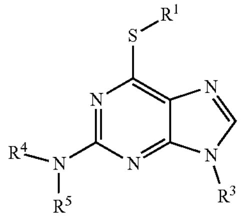

in which $R^1$ and $R^5$ are as defined above, $R^3$ is a $(C_1-C_6)$alkyl group, a $(C_1-C_6)$cycloalkyl group, an aryl group, a —$CH_2$-aryl group or a —$CH_2$-heteroaryl group, said alkyl, cycloalkyl, aryl and heteroaryl group being optionally substituted with one or more substituents chosen from a halogen atom, a hydroxyl group and a $NH_2$ group, $R^4$ is a hydrogen atom, a $(C_1-C_6)$alkyl group or a $(C_1-C_6)$cycloalkyl group, said alkyl and cycloalkyl group being optionally substituted with one or more substituents chosen from a halogen atom, a hydroxyl group and a $NH_2$ group, and their addition salts with pharmaceutically acceptable acids.

According to a particular embodiment, the present invention relates to a compound of formula (Ie), as defined above, for use according to the present invention, in which, $R^1$ is a —$CH_2$-aryl group, preferably a benzyl group, $R^3$ is a $(C_1-C_6)$alkyl group, preferably an isopropyl group, $R^4$ is a hydrogen atom, $R^5$ is a $(C_1-C_6)$alkyl group being optionally substituted with one or more hydroxyl group, preferably $R^5$ is a 1-hydroxybutan-2-yl group, and its addition salts with pharmaceutically acceptable acids.

Compound 47 as defined herein after in Table 1, and its pharmaceutically acceptable salts, are in particular encompassed within the scope of formula (Ie).

The compounds of formulae (I), (Ia), (Ib), (Ic), (Id) and (Ie) can comprise one or more asymmetric carbon atoms. They can thus exist in the form of enantiomers or of diastereoisomers. These enantiomers, diastereoisomers and their mixtures, including the racemic mixtures, form part of the invention.

The pharmaceutically acceptable salts of the compounds of formulae (I), (Ia), (Ib), (Ic), (Id) and (Ie) include the addition salts with pharmaceutically acceptable acids, such as inorganic acids, for example hydrochloric, hydrobromic, phosphoric or sulphuric acid and organic acids, such as acetic, trifluoroacetic, propionic, oxalic, succinic, fumaric, malic, tartaric, citric, ascorbic, maleic, glutamic, benzoic, toluenesulphonic, methanesulphonic, stearic and lactic acid.

The compounds of formulae (I), (Ia), (Ib), (Ic), (Id) and (Ie) or their salts can form solvates (namely hydrates); the invention includes such solvates.

Therefore, the present invention furthermore concerns a compound of formula (I) according to the disclosed invention herein, wherein M represents a $NR^1R^2$ group or an $OR^1$ group, $R^1$ is an aryl group, a heteroaryl group, a —$CH_2$-aryl group or a —$CH_2$-heteroaryl group, said aryl and heteroaryl being optionally substituted with one or more substituents independently chosen from a halogen atom, a $CF_3$ group, a hydroxyl group, an $OR^6$ group, a $SR^6$ group, a $NR^6R^7$ group, a CN group, a $CONR^6R^7$ group, a $SOR^6$ group, a $SO_2R^6$ group, an azido group (—$N_3$), an aryl group, a heteroaryl group and a ($C_1$-$C_6$)alkyl group, and preferably $R^1$ is an aryl group, a heteroaryl group, a —$CH_2$-aryl group or a —$CH_2$-heteroaryl group, said aryl and heteroaryl being optionally substituted with one halogen atom or a $CF_3$ group, $R^6$ and $R^7$ represent independently of each other a hydrogen atom or a ($C_1$-$C_6$)alkyl group, and $R^2$ is a ($C_1$-$C_6$)alkyl group or a ($C_1$-$C_6$)cycloalkyl group said alkyl and cycloalkyl group being optionally substituted with one or more substituents independently chosen from a halogen atom, a hydroxyl group and a $NH_2$ group, and preferably $R^2$ is a ($C_1$-$C_6$)alkyl group, and its addition salts with pharmaceutically acceptable acids, for use according to the present invention.

In some embodiments, M represents a $NR^1R^2$ group, and said $NR^1R^2$ radical is chosen from the following radicals:

(1)

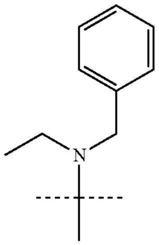

(2)

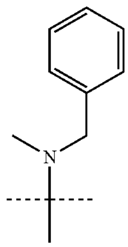

(15)

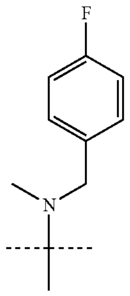

(17)

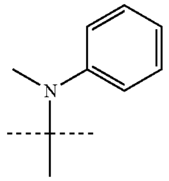

(25)

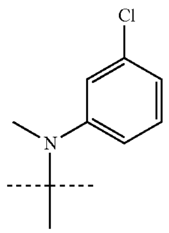

-continued (43)

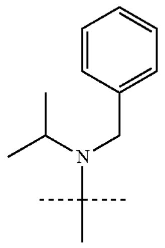

and (44)

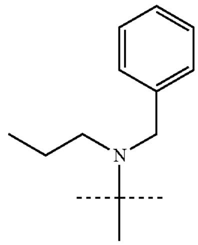

, and their addition salts with pharmaceutically acceptable acids, for use according to the present invention.

In some embodiments, the compound of formula (I) may be characterised in that:

A represents a $NR^4R^5$ group, $R^4$ is a hydrogen atom, $R^5$ is a ($C_1$-C8) alkyl group, said alkyl group being optionally substituted with one or more substituents independently chosen from a halogen atom, a hydroxyl group, a —$OCOR^a$ group and a $NR^6R^7$ group, one or more of the carbon atoms of said alkyl group being optionally replaced by a nitrogen atom, $R^5$ being preferably a ($C_1$-$C_6$)alkyl group, said alkyl group being optionally substituted with one hydroxyl group, and one of the carbon atoms of said alkyl group being optionally replaced by a nitrogen atom, $R^a$ represents a ($C_1$-$C_6$)alkyl group, said alkyl group being optionally substituted by an amino group, or alternatively $R^4$ and $R^5$ may form with the nitrogen atom bearing them a ($C_3$-$C_6$) heterocylcoalkyl group, said ($C_3$-$C_6$) heterocylcoalkyl group being optionally substituted by one or more substituents independently chosen from a ($C_1$-$C_4$)alkyl group, a $NR^6R^7$ group and a halogen atom, and $R^6$ and $R^7$ represent independently of each other a hydrogen atom or a ($C_1$-$C_6$)alkyl group, and its addition salts with pharmaceutically acceptable acids.

In some embodiments, A represents a group a $NR^4R^5$ group selected from the following radicals:

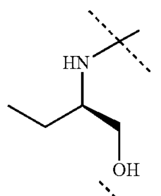

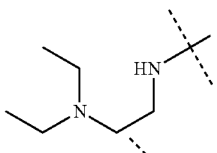

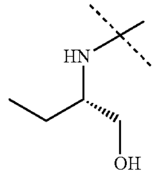

and

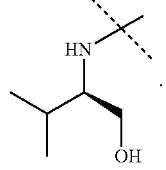

.

In some embodiments, the compound of formula (I) may be characterized in that:

$R^3$ is a $(C_1\text{-}C_6)$alkyl group, a $(C_1\text{-}C_6)$cycloalkyl group, an aryl group or a —$CH_2$-aryl group, said alkyl, cycloalkyl and aryl group being optionally substituted with one or more substituents independently chosen from a halogen atom, a hydroxyl group and a $NH_2$ group, and preferably $R^3$ represents a cyclopentyl group, an isopropyl group or a benzyl group.

More specific compounds are gathered in the following table, which may be used in the framework of the present invention.

TABLE 1

| No | Structure |
|---|---|
| Aftin-1 | 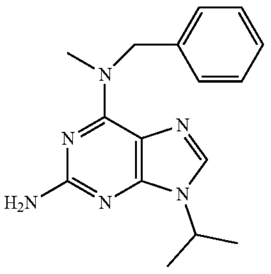 [SMILES: CC(C)n1cnc2c(N(C)Cc3ccccc3)nc(N)nc21] |
| Aftin-2 | 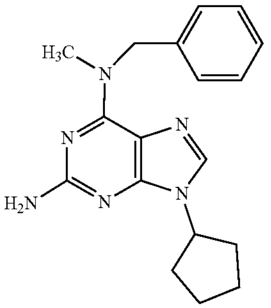 [SMILES: CN(Cc1ccccc1)c1nc(N)nc2c1ncn2C1CCCC1] |
| Aftin-3 | 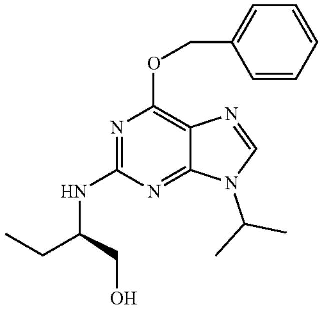 [SMILES: CC[C@H](CO)Nc1nc(OCc2ccccc2)c2ncn(C(C)C)c2n1] |
| Aftin-4 | 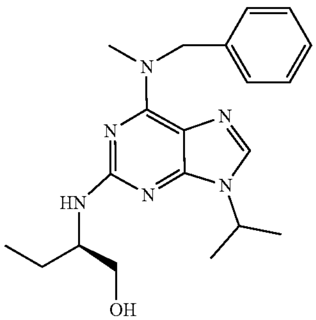 [SMILES: CC[C@H](CO)Nc1nc(N(C)Cc2ccccc2)c2ncn(C(C)C)c2n1] |

TABLE 1-continued

| No | Structure |
|---|---|
| Aftin-5 | 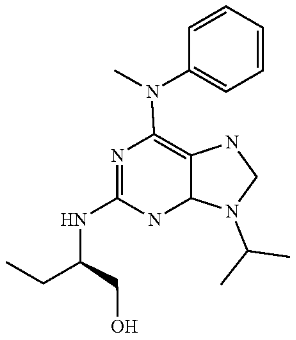 |
| 8 | 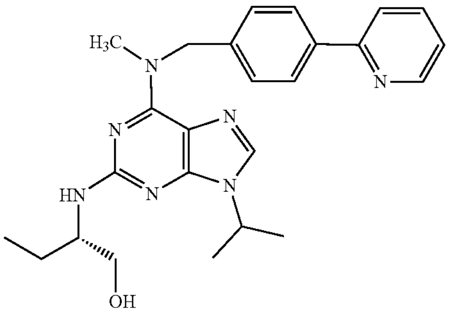 [SMILES: CC[C@@H](CO)Nc1nc(N(C)Cc2ccc(-c3ccccn3)cc2)c2ncn(C(C)C)c2n1] |
| 9 | 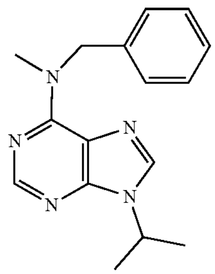 [SMILES: CC(C)n1cnc2c(N(C)Cc3ccccc3)ncnc21] |
| 12 | 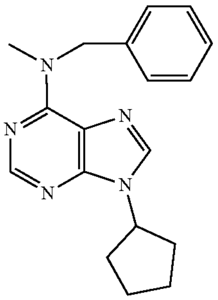 [SMILES: CN(Cc1ccccc1)c1ncnc2c1ncn2C1CCCC1] |
| 13 | 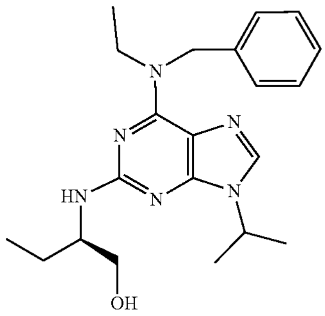 [SMILES: CC[C@H](CO)Nc1nc(N(CC)Cc2ccccc2)c2ncn(C(C)C)c2n1] |

TABLE 1-continued
| No | Structure |
|---|---|
| 14 | 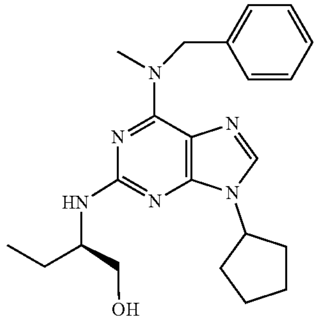 [SMILES: CC[C@H](CO)Nc1nc(N(C)Cc2ccccc2)c2ncn(C3CCCC3)c2n1] |
| 15 | 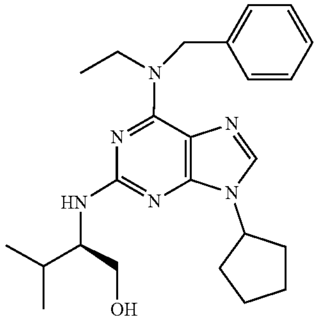 [SMILES: CCN(Cc1ccccc1)c1nc(N[C@@H](CO)C(C)C)nc2c1ncn2C1CCCC1] |
| 16 | 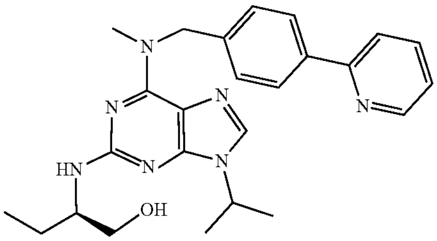 [SMILES: CC[C@H](CO)NC(=N)/N=C(\c1ncn(C(C)C)c1C)N(C)Cc1ccc(-c2ccccn2)cc1] |
| 17 | 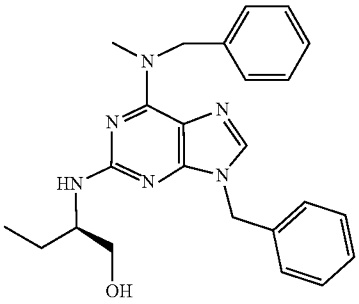 [SMILES: CC[C@H](CO)NC(=N)/N=C(\c1ncn(Cc2ccccc2)c1C)N(C)Cc1ccccc1] |
| 18 | 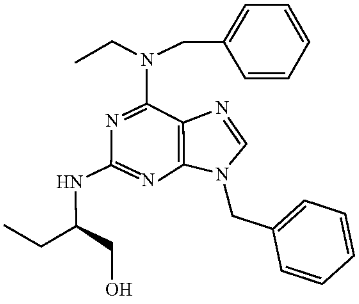 [SMILES: CC[C@H](CO)NC(=N)/N=C(\c1ncn(Cc2ccccc2)c1C)N(CC)Cc1ccccc1] |
| 19 | 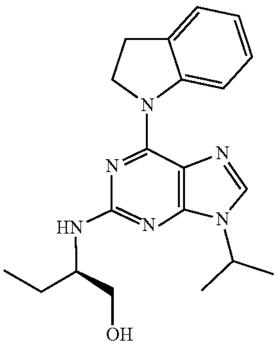 [SMILES: CC[C@H](CO)NC(=N)/N=C(\c1ncn(C(C)C)c1C)N1CCc2ccccc21] |
| 20 | 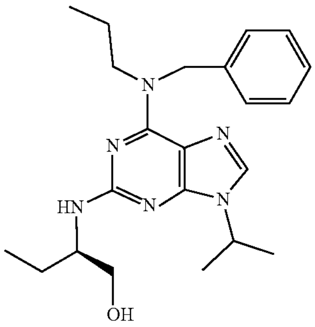 [SMILES: CCCN(Cc1ccccc1)/C(=N/C(=N)N[C@H](CC)CO)c1ncn(C(C)C)c1C] |
| 21 | 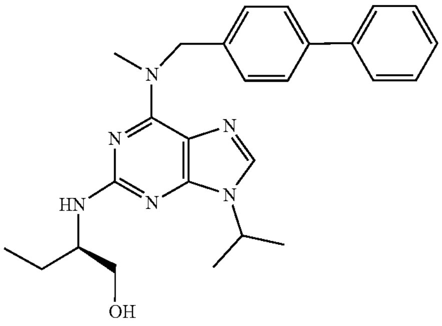 [SMILES: CC[C@H](CO)Nc1nc(N(C)Cc2ccc(-c3ccccc3)cc2)c2ncn(C(C)C)c2n1] |
| 22 | 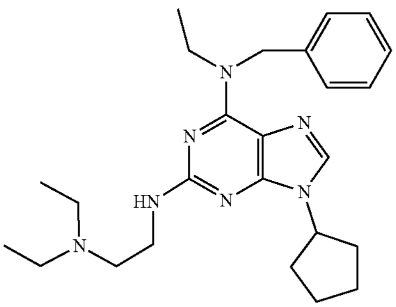 [SMILES: CCN(CC)CCNc1nc(N(CC)Cc2ccccc2)c2ncn(C3CCCC3)c2n1] |

TABLE 1-continued
| No | Structure |
| --- | --- |
| 23 | 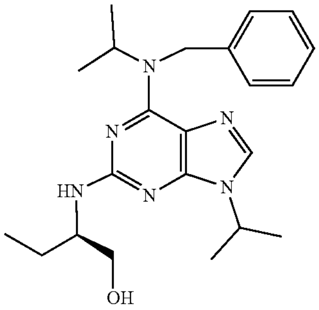 [SMILES: CC[C@H](CO)Nc1nc(N(Cc2ccccc2)C(C)C)c2ncn(C(C)C)c2n1] |
| 24 | 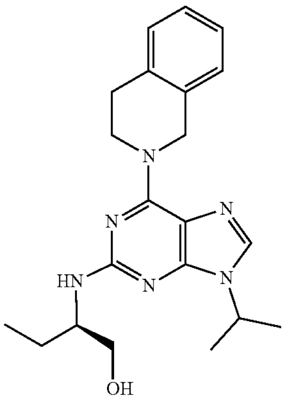 [SMILES: CC[C@H](CO)Nc1nc(N2CCc3ccccc3C2)c2ncn(C(C)C)c2n1] |
| 26 | 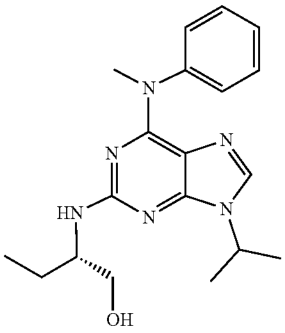 [SMILES: CC[C@@H](CO)Nc1nc(N(C)c2ccccc2)c2ncn(C(C)C)c2n1] |
| 28 | 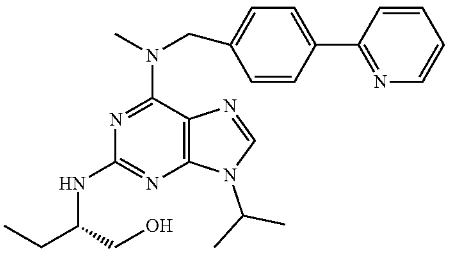 [SMILES: CC[C@@H](CO)Nc1nc(N(C)Cc2ccc(-c3ccccn3)cc2)c2ncn(C(C)C)c2n1] |
| 29 | 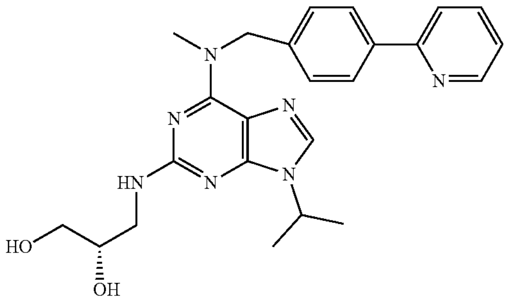 [SMILES: CC(C)n1cnc2c(N(C)Cc3ccc(-c4ccccn4)cc3)nc(NC[C@H](O)CO)nc21] |
| 31 | 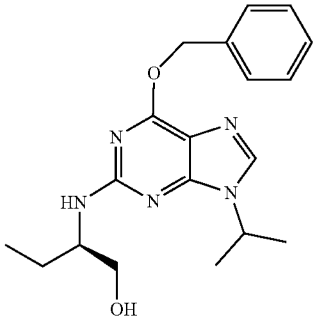 [SMILES: CC[C@H](CO)Nc1nc(OCc2ccccc2)c2ncn(C(C)C)c2n1] |
| 32 | 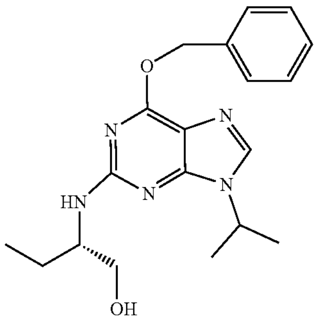 [SMILES: CC[C@@H](CO)Nc1nc(OCc2ccccc2)c2ncn(C(C)C)c2n1] |
| 33 | 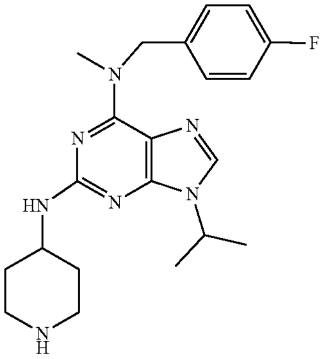 [SMILES: CC(C)n1cnc2c(N(C)Cc3ccc(F)cc3)nc(NC3CCNCC3)nc21] |
| 34 | 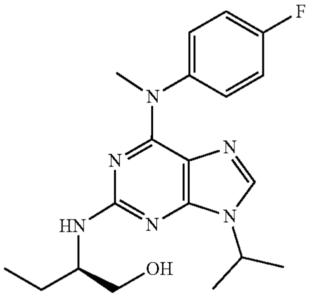 [SMILES: CC[C@H](CO)Nc1nc(N(C)c2ccc(F)cc2)c2ncn(C(C)C)c2n1] |

TABLE 1-continued
| No | Structure |
|---|---|
| 35 | 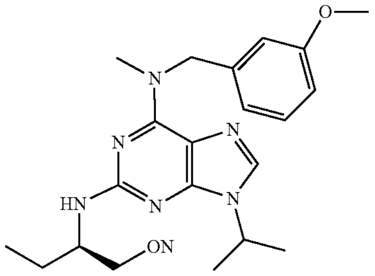 |
| 36 | 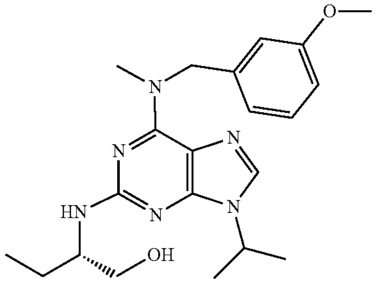 [SMILES: CC[C@@H](CO)Nc1nc(N(C)Cc2cccc(OC)c2)c2ncn(C(C)C)c2n1] |
| 37 | 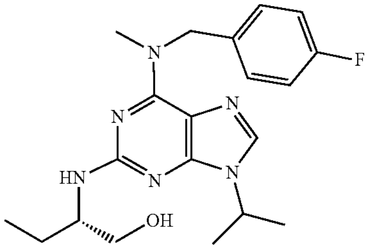 [SMILES: CC[C@@H](CO)Nc1nc(N(C)Cc2ccc(F)cc2)c2ncn(C(C)C)c2n1] |
| 38 | 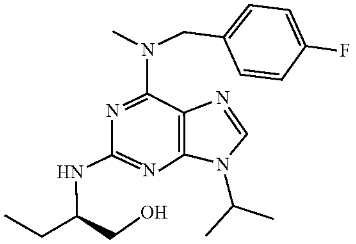 [SMILES: CC[C@H](CO)NC(=N)/N=C(\c1ncn(C(C)C)c1C)N(C)Cc1ccc(F)cc1] |
| 39 | 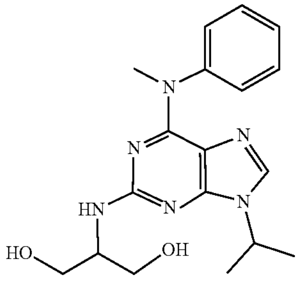 [SMILES: Cc1c(/C(=N\C(=N)NC(CO)CO)N(C)c2ccccc2)ncn1C(C)C] |
TABLE 1-continued
| No | Structure |
|---|---|
| 40 | 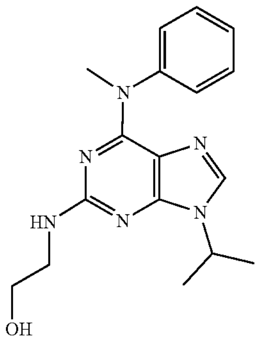 [SMILES: CC(C)n1cnc2c(N(C)c3ccccc3)nc(NCCO)nc21] |
| 41 | 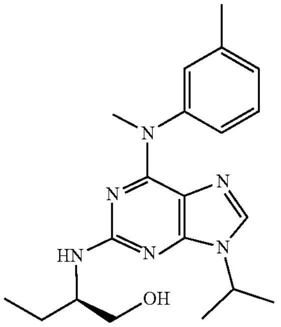 [SMILES: CC[C@H](CO)NC(=N)/N=C(\c1ncn(C(C)C)c1C)N(C)c1cccc(C)c1] |
| 42 | 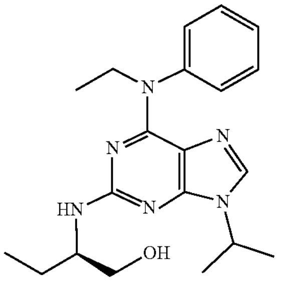 [SMILES: CC[C@H](CO)NC(=N)/N=C(\c1ncn(C(C)C)c1C)N(CC)c1ccccc1] |
| 43 | 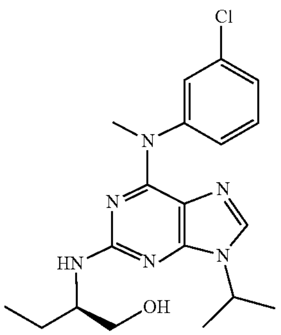 [SMILES: CC[C@H](CO)NC(=N)/N=C(\c1ncn(C(C)C)c1C)N(C)c1cccc(Cl)c1] |

TABLE 1-continued

| No | Structure |
|---|---|
| 44 | 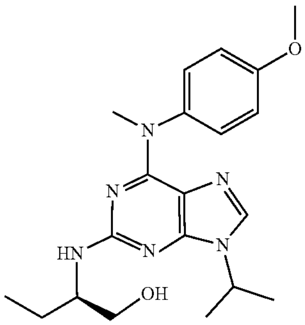 [SMILES: CC[C@H](CO)NC(=N)/N=C(\c1ncn(C(C)C)c1C)N(C)c1ccc(OC)cc1] |
| 45 | 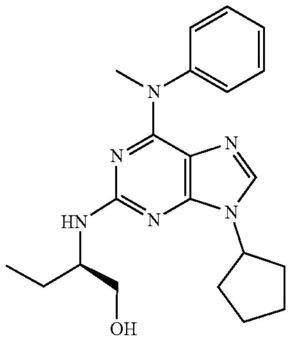 [SMILES: CC[C@H](CO)Nc1nc(N(C)c2ccccc2)c2ncn(C3CCCC3)c2n1] |
| 46 | 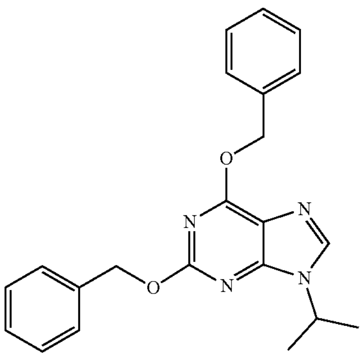 [SMILES: CC(C)n1cnc2c(OCc3ccccc3)nc(OCc3ccccc3)nc21] |
| 47 | 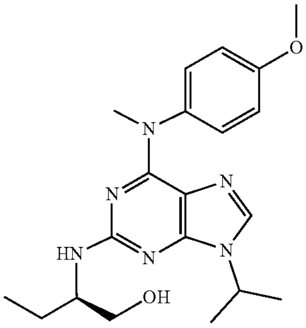 [SMILES: CC[C@H](CO)Nc1nc(N(C)c2ccc(OC)cc2)c2ncn(C(C)C)c2n1] |

TABLE 1-continued

| No | Structure |
|---|---|
| 48 | 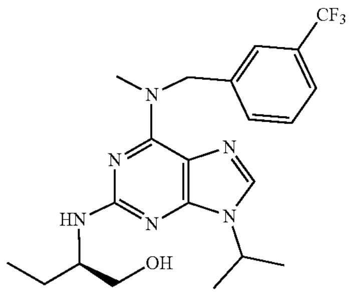 [SMILES: CC[C@H](CO)Nc1nc(N(C)Cc2cccc(C(F)(F)F)c2)c2ncn(C(C)C)c2n1] |
| 49 | 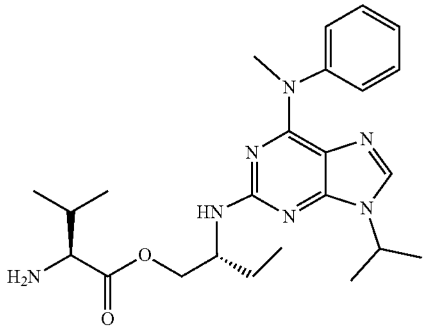 [SMILES: CC[C@H](COC(=O)[C@@H](N)C(C)C)Nc1nc(N(C)c2ccccc2)c2ncn(C(C)C)c2n1] |
| 50 | 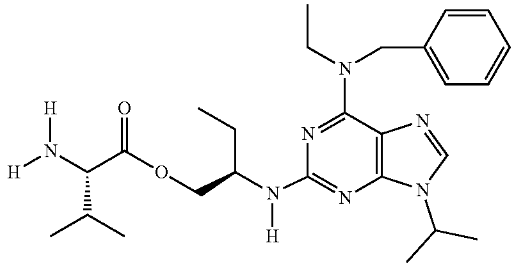 [SMILES: CC[C@H](COC(=O)[C@@H](N)C(C)C)Nc1nc(N(CC)Cc2ccccc2)c2ncn(C(C)C)c2n1] |

According to a preferred embodiment of the present invention, the compound of formula (I) for use according to the present invention is selected from those disclosed in Table 1 herein above, and is in particular a compound selected from compound 13, 14, 15, 18, 20, 22, 23, 26, 31, 38 and Aftin-5, and more particularly is Aftin-5 and compound 13.

Illustratively, the compound of formula (I) for use according to the present invention is selected from compound of formula:

(Aftin-5)

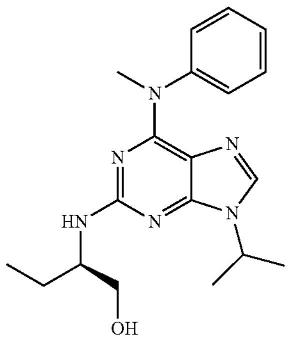

,

-continued
(13)
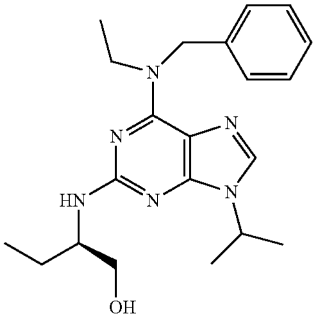
,
(14)
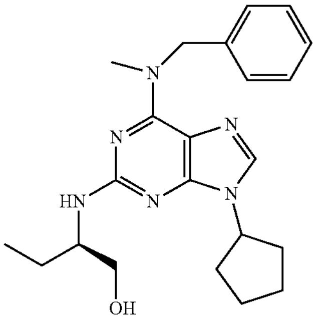
,
(15)
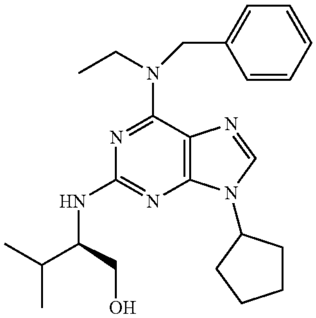
,
(18)
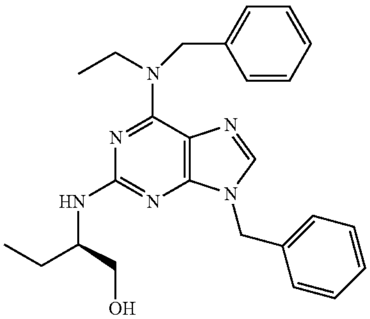
,
(20)
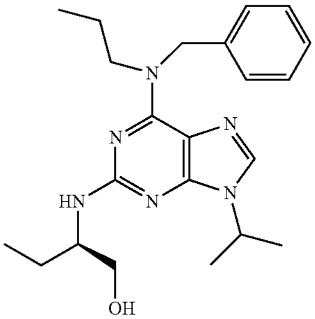
,
-continued
(22)
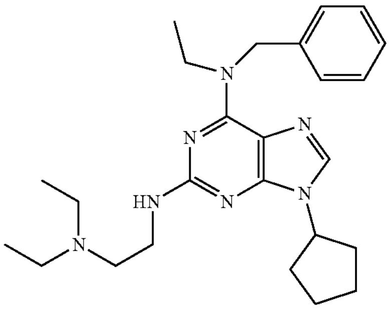
,
(23)
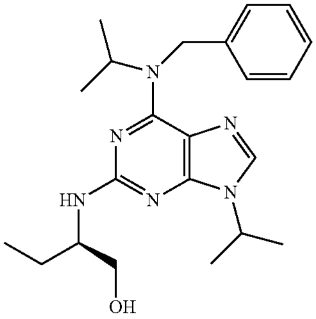
,
(26)
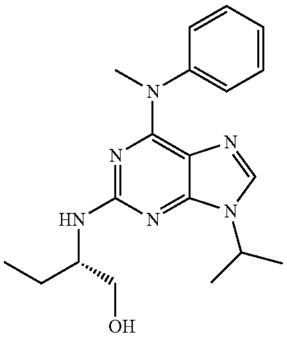
,
(31)
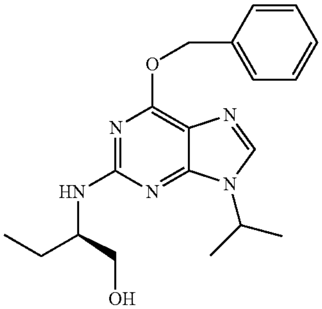
, and
(38)
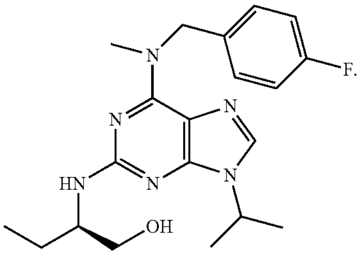
The compounds of formula (I) may be prepared according to any suitable method from the state in the art, e.g. the preparation procedures described in EP 2 664 619 and variant of these procedures, which may be implemented starting from the knowledge of a skilled artisan.

New Compounds of Formula (I)

The present invention further relates to a subclass of compounds of formula (I), as defined herein after, which are new.

The present invention more particularly relates to a compound of formula (I)

(I)

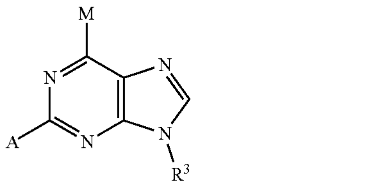

in which

M represents a $NR^1R^2$ group, an $OR^1$ group or a $SR^1$ group,

A represents a $NR^4R^5$ group, $R^1$ is an aryl group, a heteroaryl group, a —$CH_2$-aryl group or a —$CH_2$-heteroaryl group, said aryl and heteroaryl being optionally substituted with one or more substituents independently chosen from a halogen atom, a $CF_3$ group, a hydroxyl group, an $OR^6$ group, a $SR^6$ group, a $NR^6R^7$ group, a CN group, a $CONR^6R^7$ group, a $SOR^6$ group, a $SO_2R^6$ group, an azido group (—$N_3$), an aryl group, a heteroaryl group and a ($C_1$-$C_6$)alkyl group, $R^2$ is a ($C_1$-$C_6$)alkyl group or a ($C_1$-$C_6$)cycloalkyl group said alkyl and cycloalkyl group being optionally substituted with one or more substituents independently chosen from a halogen atom, a hydroxyl group and a $NH_2$ group, or $R^1$ forms together with $R^2$ and with the nitrogen atom that bears $R^1$ and $R^2$ an heterobicyclic ring, $R^6$ and $R^7$ represent independently of each other a hydrogen atom or a ($C_1$-$C_6$)alkyl group, $R^3$ is a ($C_1$-$C_6$)alkyl group, a ($C_1$-$C_6$)cycloalkyl group, an aryl group, a —$CH_2$-aryl group, a $CH_2$-($C_1$-$C_6$)cycloalkyl group or a —$CH_2$-heteroaryl group, said alkyl, cycloalkyl, aryl and heteroaryl group being optionally substituted with one or more substituents independently chosen from a halogen atom, a hydroxyl group and a $NH_2$ group, $R^4$ is a hydrogen atom, a ($C_1$-$C_6$)alkyl group, a ($C_1$-$C_6$) cycloalkyl group, an aryl group or a heteroaryl group, said alkyl and cycloalkyl group being optionally substituted with one or more substituents independently chosen from a halogen atom, a hydroxyl group and a $NH_2$ group, said aryl and heteroaryl being optionally substituted with one or more substituents chosen from a halogen atom, a hydroxyl group, a $NH_2$ group and a NH—$R^9$ group, $R^9$ is a heteroaryl group optionally substituted with one or more substituents chosen from a halogen atom, a hydroxyl group, a $NH_2$ group and a heteroaryl group, $R^5$ is a ($C_1$-$C_8$)alkyl group or a ($C_1$-$C_6$)cycloalkyl group, said alkyl and cycloalkyl group being substituted with one, two or three —$OCOR^a$ group(s), or with one, two or three —$OP(O)(OH)OR^a$ group(s), one or more of the carbon atoms of said alkyl or cycloalkyl group being optionally replaced by a nitrogen atom, $R^a$ represents a ($C_1$-$C_6$)alkyl group, said alkyl group being optionally substituted by an amino group, $R^{10}$ is a hydrogen atom, a ($C_1$-$C_6$)alkyl group, a ($C_1$-$C_6$) cycloalkyl group, an aryl group, a heteroaryl group, a —$CH_2$-aryl group or —$CH_2$-heteroaryl group, said aryl being optionally substituted with one or more substituents chosen from a halogen atom, a hydroxyl group, an $OR^6$ group, a $SR^6$ group, a $NR^6R^7$ group, a CN group, a $CONR^6R^7$ group, a $SO_2NR^6R^7$ group, a $SOR^6$ group, a $SO_2R^6$ group and an azido group ($N_3$), and its addition salts with pharmaceutically acceptable acids.

In other words, the $R^5$ radical necessarily includes an ester, which may be derived from natural or non natural amino acids.

According to a particular embodiment, the present invention relates to said new compound of formula (I) as defined above, wherein $R^5$ is a ($C_1$-$C_8$)alkyl group being substituted with one —$OCOR^a$ group, one or more of the carbon atoms of said alkyl group being optionally replaced by a nitrogen atom, $R^a$ represents a ($C_1$-$C_6$)alkyl group, said alkyl group being optionally substituted by an amino group, and its addition salts with pharmaceutically acceptable acids.

According to an even more particular embodiment, the present invention relates to a compound of formula (I) selected from (49)

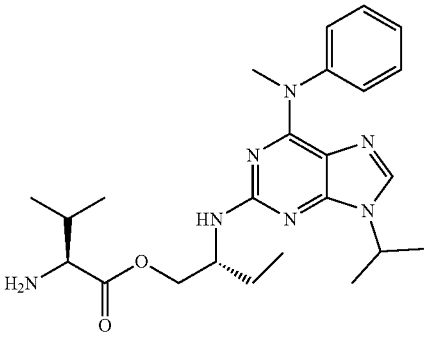

and (50)

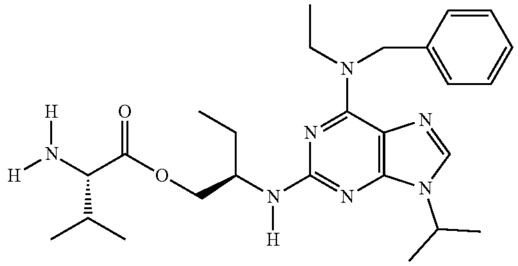

and their addition salts with pharmaceutically acceptable acids, as inorganic acids, for example hydrochloric, hydrobromic, phosphoric or sulphuric acid and organic acids, such as acetic, trifluoroacetic, propionic, oxalic, succinic, fumaric, malic, tartaric, citric, ascorbic, maleic, glutamic, benzoic, toluenesulphonic, methanesulphonic, stearic and lactic acid.

Typically, the said new compounds of formula (I), bearing a —$OCOR^a$ group, may be synthetized via an esterification step, according to common practice, well known to the man skilled in the art, starting form a compound of formula (I) bearing a OH group in its $R^5$ radical. Examples 3 and 4 herein after illustrate these new compounds.

Such compounds of formula (I) may be prodrugs forming active or non-active metabolites when administered to the patients.

Uses

The compounds of formula (I), any one of the other sub-formulas as defined above or any one of their pharmaceutically acceptable salts may be used in the treatment of non-traumatic acquired brain injuries (ABI).

An acquired brain injury (ABI) is an injury to the brain that is not hereditary, congenital, degenerative, or induced by birth trauma. Essentially, this type of brain injury is one that has occurred after birth. The injury results in a change to the brain's neuronal activity, which affects the physical integrity, metabolic activity, or functional ability of nerve cells in the brain.

In other words, neurodegenerative diseases such as Alzheimer's disease, Parkinson's disease, Huntington's disease, amyotrophic lateral sclerosis, and is more particularly Alzheimer's disease are clearly not encompassed within the scope of the present invention.

There are two types of ABIs as defined by the Brain Injury Association: Traumatic brain injuries (TBI) and Non-traumatic brain injuries.

A traumatic brain injury (TBI) is defined as an alteration in brain function, or other evidence of brain pathology, caused by an external force. Traumatic impact injuries can be defined as closed (or non-penetrating) or open (penetrating). They generally result from mechanical impact or acceleration-deceleration insults that cause skull fractures, compression of cerebral tissues, and tearing of white and gray matter and subsequent hemorrhage (Bramlett et al., Journal of Cerebral Blood Flow & Metabolism, 24: 133-150, 2004)

There are two primary mechanisms of TBI: those involving impact to the head (traumatic impact) and those involving inertial forces which affect the brain (traumatic interial). Examples of TBI include falls, assaults, motor vehicle accidents and sport injuries. Different forms of lesions may be produced by a TBI among all contusive, concessive, diffuse axonal injury and haemorrhagic lesions.

A Non-traumatic brain injury is an alteration in brain function or pathology caused by an internal force. These can be caused by strokes (Hemorrhage, Blood Clot), infectious diseases (Meningitis, Encephalitis), seizures, electric shocks, tumors, toxic exposure, metabolic disorders, neurotoxic poisoning (Carbon Monoxide, Lead Exposure), lack of oxygen (Drowning, Choking, Hypoxic/Anoxic Injury), or drug overdoses.

According to one embodiment, the present invention mainly focuses on non-traumatic brain injuries, and in particular focuses on hypoxic injuries, and more particularly on neonatal hypoxia-ischemia (HI) and neonatal hypoxic-ischemic encephalopathy (HIE).

These conditions commonly result from birth asphyxia which causes severe reductions in cerebral blood flow (CBF) and leads to deprivations in oxygen and glucose delivery, as well as the build-up of potentially toxic substances Typically, a non-traumatic acquired brain injury (ABI) is caused by stroke (i.e. embolism, thrombosis, aneurysm), tumor, bleeding in the brain (intracranial surgery, hemorrhage, hematoma), infectious disease that affects the brain (i.e. meningitis), toxic exposure (carbon monoxide poisoning, inhaling toxic chemicals, solvent sniffing, excessive and prolonged use of drugs and/or alcohol) or lack of oxygen supply to the brain (i.e., heart attack, near drowning, anoxia/hypoxia, drug overdose).

In one embodiment, a non-traumatic acquired brain injury (ABI) is caused by brain tumours, metabolic disorders, toxic exposure, arteriovenous malformation in brain vasculature, brain haemorrhage, status epilepticus, diabetes, alcohol and/or drug intake, hypoxic brain injury/anoxic brain injury, hypoxia-ischemia, hypoxic-ischemic encephalopathy, diffuse cerebral hypoxia, focal cerebral ischemia, cerebral infarction global cerebral ischemia, and brain encephalopathy.

In one embodiment, a non-traumatic acquired brain injury (ABI) may typically be caused by pressure from a tumor, lack of oxygen or exposure to at least a toxin.

According to another embodiment, the use conform to the present invention is directed to the treatment of acquired brain injuries caused by oxygen deficiency.

According to a particular embodiment, the non-traumatic acquired brain injury is a hypoxic injury.

According to another particular embodiment, the non-traumatic acquired brain injury is a neonatal encephalopathy, including neonatal hypoxia-ischemia (HI) and neonatal hypoxic-ischemic encephalopathy (HIE).

A HIE injury is a result of an insufficient blood flow to the brain combined with a lower-than-normal concentration of oxygen in arterial blood. This event in the immature and developing brain can cause significant mortality and result in long term neurological deficits such as cerebral palsy, epilepsy, severe learning and mental impairments, cognitive developmental problems and motor and behavioral problems.

It has been observed that following a brain insult in particular caused by oxygen deficiency, the BBB permeability is affected.

Namely, abnormalities in BBB permeability after HI are multifactorial and involve factors such as energy depletion, release of reactive oxygen species (ROS) and local inflammation (Riljak, V., et al., Pathophysiology of Perinatal Hypoxic-Ischemic Encephalopathy-Biomarkers, Animal Models and Treatment Perspectives, *Physiological Research,* 2016, 65: p. S533-S545; del Zoppo, G. J., Inflammation and the neurovascular unit in the setting of focal cerebral ischemia, *Neuroscience,* 2009, 158(3): p. 972-982.). These damages are observed early (hours to days) after an HI insult.

On the basis of the biological activities as illustrated in the experimental data herein after, said compound of formula (I) may be used for treating any one of the disorders as mentioned above.

Aftin compounds were previously disclosed in WO2018/189122 as having a positive impact on some of the hallmarks associated with Alzheimer Disease (AD) and therefore as being useful for treating a neurodegenerative disorder and/or a neuro-inflammatory disorders.

The inventors have now unexpectedly demonstrated that said Aftin compounds present the capacity of decreasing and/or repairing brain injury lesions. This was never disclosed before. Indeed, WO2018/189122 only demonstrated that Aftin-5 was able to cross the BBB, but no repairing action on the brain was disclosed nor suggested. As it will emerge from the 'Examples' section below, the experimental data provide converging evidence in favour of the use of a compound of formula (I), such as e.g. Aftin-5 and compound 13, to efficiently repair and/or decrease the brain injury lesions, in particular caused by oxygen deficiency.

Thus, according to one embodiment, the present invention relates to a compound of formula (I) for use as defined above, wherein said compound of formula (I) decreases and/or repairs brain injury lesions, in particular caused by oxygen deficiency.

According to a preferred embodiment of the present invention, the compound of formula (I) selected from those disclosed in Table 1 herein above, or one of its pharmaceutically acceptable salts, in particular a compound selected from compound 13, 14, 15, 18, 20, 22, 23, 26, 31, 38 and Aftin-5, and more particularly is Aftin-5 and compound 13, is for use in the treatment of neonatal encephalopathy, including neonatal hypoxia-ischemia (HI) and neonatal hypoxic-ischemic encephalopathy (HIE).

Surprisingly, in the well-characterized Rice-Vannucci neonatal HI model, the inventors demonstrated consistent decrease of the brain injury lesions (FIG. 1) and increase of neurotrophic markers in the brain after administration of Aftin compounds. They confirmed that Aftins help reduce neurovascular alterations and brain injuries and could prevent long term negative outcomes. In addition, in vitro studies on a rodent Blood Brain Barrier (BBB) model showed that this family of molecules is able to cross the BBB, to be distributed to the brain parenchyma and to reverse BBB leakage under inflammatory stress (FIG. 2).

In one aspect, the present invention further relates to the use of at least a compound of formula (I), any one of the other sub-formulae as defined above or any one of its pharmaceutically acceptable salts for the manufacture of a pharmaceutical composition intended for the treatment of non-traumatic acquired brain injury (ABI), in particular in the treatment of hypoxic injuries, and more particularly in the treatment of neonatal hypoxia-ischemia (HI) and neonatal hypoxic-ischemic encephalopathy (HIE).

In another aspect, the present invention relates to a method for treating non-traumatic acquired brain injury (ABI), in particular in the treatment of hypoxic injuries, and more particularly in the treatment of neonatal hypoxia-ischemia (HI) and neonatal hypoxic-ischemic encephalopathy (HIE) in an individual in need thereof, comprising the administration of an effective amount of a compound of formula (I), any one of the other sub-formulae as defined above or any one of its pharmaceutically acceptable salts, optionally in a pharmaceutically acceptable vehicle.

In particular, an individual in need thereof is an individual suffering from a non-traumatic acquired brain injury (ABI), in particular from hypoxic injuries, and more particularly from neonatal hypoxia-ischemia (HI) or neonatal hypoxic-ischemic encephalopathy (HIE). In a particular embodiment, said individual is an infant. Preferably, said infant is a neonate.

The compound of formula (I) may be implemented in any type of pharmaceutical composition.

The formulation of pharmaceutical compositions comprising at least one compound of formula (I) or any one of the sub-formulae as defined above, according to the instant invention may be prepared according to the well-known principles and techniques applicable in the art.

In some embodiments, a suitable pharmaceutically acceptable vehicle according to the invention includes any and all conventional solvents, dispersion media, fillers, solid carriers, aqueous solutions, coatings, antibacterial and antifungal agents, isotonic and absorption delaying agents, and the like.

In certain embodiments, suitable pharmaceutically acceptable vehicles may include, water, saline, phosphate buffered saline, dextrose, glycerol, ethanol and a mixture thereof.

In some embodiments, pharmaceutically acceptable vehicles may further comprise minor amounts of auxiliary substances or excipients such as wetting or emulsifying agents, preservatives or buffers, which enhance the shelf life or effectiveness of the active ingredient. The preparation and use of pharmaceutically acceptable vehicles is well known in the art. The aforementioned excipients are selected according to the dosage form and the desired mode of administration.

With the express exception of any conventional media or agent incompatible with the active ingredient, use thereof in the pharmaceutical compositions of the present invention is contemplated.

In some embodiments, the active agent, e.g. in the form of a pharmaceutic composition may be administered by any suitable route, including enteral (e.g. , oral), parenteral, intravenous, intramuscular, intra-arterial, intramedullary, intrathecal, subcutaneous, intraventricular, transdermal, intradermal, rectal, intravaginal, intraperitoneal, topical, mucosal, nasal, buccal, sublingual; by intratracheal instillation, bronchial instillation, and/or inhalation; and/or as an oral spray, nasal spray, and/or aerosol.

In some embodiments, the active agent is administered by oral administration or systemic intravenous administration.

In certain embodiments, the administration of the pharmaceutical composition by injection may be directly performed in the target tissue of interest, in particular in order to avoid spreading of the said active ingredient in the pharmaceutical composition.

Other modes of administration employ pulmonary formulations, suppositories, and transdermal applications.

In some embodiments, an oral formulation according to the invention includes usual excipients, such as, for example, pharmaceutical grades of mannitol, lactose, starch, magnesium stearate, sodium saccharine, cellulose, magnesium carbonate, and the like.

In some embodiments, an effective amount of said compound is administered to said individual in need thereof.

It is within the common knowledge of a skilled artisan to determine the effective amount of a compound of formula (I), as the active ingredient to observe the desired outcome.

Within the scope of the instant invention, the effective amount of the compound to be administered may be determined by a physician or an authorized person skilled in the art and can be suitably adapted within the time course of the treatment.

In certain embodiments, the effective amount to be administered may depend upon a variety of parameters, including the material selected for administration, whether the administration is in single or multiple doses, and the individual's parameters including age, physical conditions, size, weight, gender, and the severity of the disorder to be treated.

In certain embodiments, an effective amount of the active agent may comprise from about 0.001 mg to about 3000 mg, per dosage unit, preferably from about 0.05 mg to about 100 mg, per dosage unit.

Within the scope of the instant invention, from about 0.001 mg to about 3000 mg includes, from about 0.002 mg, 0.003 mg, 0.004 mg, 0.005 mg, 0.006 mg, 0.007 mg, 0.008 mg, 0.009 mg, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg and 2950 mg, per dosage unit.

In certain embodiments, the active agent may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of the individual's body weight per day.

In certain embodiments, each dosage unit may be administered three times a day, two times a day, once a day, every other day, every third day, every week, every two weeks, every three weeks, or every four weeks.

In certain embodiments, the therapeutic treatment encompasses an administration of a plurality of dosage units, including two, three, four, five, six, seven, eight, nine, ten, eleven, twelve, thirteen, fourteen, or more administrations.

In certain embodiments, the treatment of the encompassed disorder may comprise the administration to the individual in need thereof of a compound of formula (I) or any one of the other sub-formulae as defined above, in combination with another compound, in particular a compound known in the art to benefit the individual in need thereof, with respect to the said disorder.

The present invention will be better understood by referring to the following examples and figures which are provided for illustrative purpose only and should not be interpreted as limiting in any manner the instant invention.

EXAMPLES

Example 1

Protocol

The study was conducted with the approval by the Institutional Animal Care and Use Committees of the Alpert Medical School of Brown University and Women & Infants Hospital of Rhode Island and in accordance with the National Institutes of Health Guidelines for the use of experimental animals.

Subjects were Wistar rats born from time-mated dams obtain from Charles River Laboratory (Wilmington, Maine, USA).

Post-natal day 7 (P7) (CNS maturation corresponding to 32-34 weeks of gestation in human) rats were assigned to 3 groups: sham, HI+PL or HI+Compound 13.

In the sham group no hypoxia-ischemia was induced in the rats. This group served as a control group.

In the HI+PL group, where PL stands for placebo, hypoxia-ischemia was induced in the rats. The rats were then further administered a saline vehicle, which served as the placebo.

In the HI+Compound 13 group, hypoxia-ischemia was induced in the rats. The rats were then further administered a dose of Compound 13, which is a compound of formula (I) according to the invention.

The Rice-Vanucci method was used to induce the HI injury (Rice J E et al., 1981) in groups HI+PL and HI+Compound 13.

In summary, each animal from all three groups was anesthetized using 3-4% isoflurane and total absence of leg withdrawal reflexes was verified prior to proceeding to surgery.

A midline ventral incision was made in the neck. The right common carotid artery (RCCA) was located and ligatured with 5-0 silk suture in groups HI+PL and HI+Compound 13. Sham subjects followed the same procedure except for an absence of RCCA ligation.

The neck incision was stitched using 5-0 silk suture. During the surgical procedure, body temperature was maintained at 36° C. using an isothermal heating pad, as reduced temperature has been shown to provide a degree of neuroprotection in humans and animal models (Marks K et al., 2010; Mishima K et al., 2004; Reinboth B S et al., 2016; Silveira R C and Procianoy R S, 2015).

Post-surgery, all rats returned to their dams for recovery during 1.5-3 h prior to hypoxia.

HI subjects from groups HI+PL and HI+Compound 13 were placed in a hypoxia chamber with 8% humidified oxygen (balanced with nitrogen) for 90 min with a chamber temperature maintained between 35-36° C. Sham subjects were exposed to room air for 90 min.

These conditions resulted in reproducible amounts of brain damage in post-natal day 10 (P10) rats (72 h post-surgery) with brain maturity equivalent of in-term newborns.

Immediately after hypoxia induction, all rats from groups HI+PL and HI+Compound 13 received an intraperitoneal (IP) injection of 30 mg/kg of either Compound 13 (HI+Compound 13 group) or an equivalent volume of vehicle (DMSO/PEG/saline) (HI+PL group).

All rats were then returned to their dam until administration of the second and third 30 mg/kg IP treatment dose of Compound 13 or vehicle 24 h and 48 h post-surgery.

72 h after HI injury (P10), the rats were euthanized, brain and blood were collected for RT-qPCR, western and bioplex analysis. Some of the pups were transcardially perfused with saline followed by 10% paraformaldehyde (PFA).

Fixed tissue was then sectioned, mounted on glass slides, stained with cresyl violet and processed for infarct volume measurement (FIG. 1B) and immunohistochemistery analysis (FIG. 1A).

The infarct was calculated as a percentage of the ratio of the damaged volume to the volume of the total contralateral hemisphere with correction for hemispheric edema, according to the following formula: infarct (%)=[1−(volume of total ipsilateral hemisphere−volume of infarct)/volume of total contralateral hemisphere)]×100%.

Results

The inventors noticed that compared to the HI+PL hemisphere, the infarct area in both males (top row) and females (bottom row) were statistically reduced after treatment with a compound of formula (I) in the HI+Compound 13 group (Statistical analysis by one-way ANOVA and Bonferroni post hoc test, *$P<0.05$; $P<0.01$; *$P<0.001$).

Example 2

Protocol

The permeability of radiolabelled sucrose ($^{14}$C-sucrose), a permeability marker, was studied on a primary rat cell-based BBB (blood-brain barrier) model. Permeability was measured in $10^{-6}$ $cm \cdot s^{-1}$. $^{14}$C-sucrose is a small molecular weight marker of 342 Da that tends to reflect paracellular disruption.

To induce increased BBB permeability, lipopolysaccharide (LPS) was injected. LPS induces increased BBB permeability by stimulating formation and release of cytokines and other molecules.

Two different Aftin compounds were tested in this example: Aftin-5 (left side of FIG. 2A) and Compound 13 (right side of FIG. 2A).

In both cases, the permeability of the non-treated BBB was used as a positive control, i.e. as a representation of the permeability of the BBB when it has not been affected by a non-traumatic ABI.

Injection of 10 ng/mL of LPS served to represent the permeability of the BBB after an inflammatory indult, such as the ones induced by non-traumatic ABIs.

Aftin-5 or Compound 13 were administered with or without LPS, at two different doses: 0.1 μM and 1 μM.

Results

The permeability test showed that administration of Aftin compounds of formula (I) according to the invention, such as Aftin-5 or Compound 13, statistically restored the permeability properties of the BBB under inflammatory stress conditions (Statistical analysis by one-way ANOVA and Dunnett' s post hoc test, *P<0.05; P<0.01; *P<0.001).

The Aftin family of molecules is able to cross the BBB to be distributed to the brain parenchyma and to reverse BBB leakage under inflammatory stress.

Conclusion

These preliminary results suggest that Aftins represent an important new class of molecules for the treatment of HIE in neonates.

Indeed, these results provide novel insights into pathways by which Aftins could restore or attenuate BBB dysfunction, improve brain metabolism and, consequently, recover neuronal function after HI insults in neonates.

This therapeutic strategy could potentially represent important adjunctive agents to hypothermia for the treatment of HIE in infants and prove efficacious to treat premature infants, for which there is currently no available treatment other than supportive care.

Example 3

Preparation of Compound 50: [(2R)-2-[[6-[benzyl(ethyl)amino]-9-isopropyl-purin-2-yl]amino]butyl] (2S)-2-amino-3-methyl-butanoate hydrochloride or L-valyl ester of (2R)-2-[[6-[benzyl(ethyl)amino]-9-isopropyl-purin-2-yl]amino]butan-1-ol hydrochloride Compound (50) was obtained as depicted in the scheme below by reacting Compound 13 with an excess of Boc-Valine HOBt ester to afford 50a. In a second step, removal of the Boc protective group was performed by using anhydrous HCl.

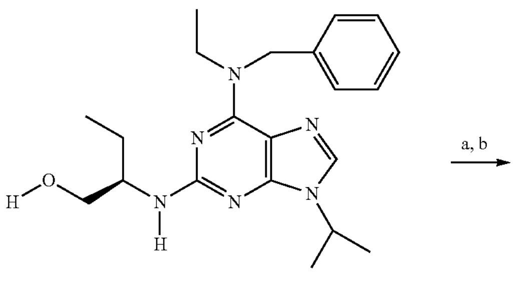

13

-continued

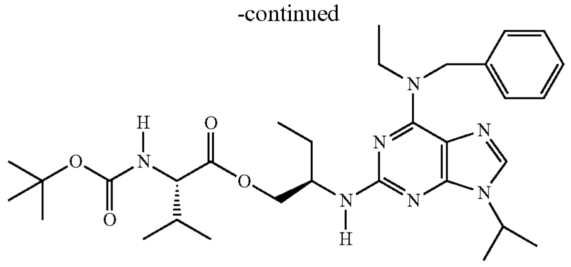

50a

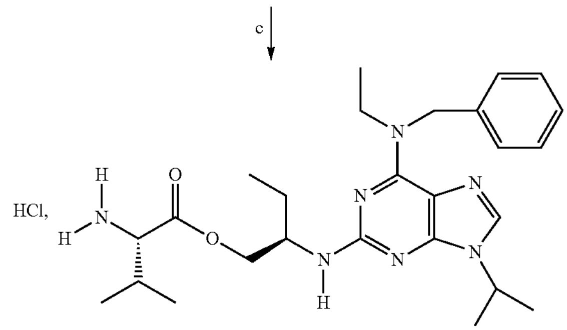

50

Reagents and conditions. a: Boc-valine, DCC, HOBt. b: compound 13, c: HCl, $Et_2O$.

[(2R)-2-[[6-[benzyl(ethyl)amino]-9-isopropyl-purin-2-yl]amino]butyl] (2S)-2-(tert-butoxycarbonylamino)-3-methyl-butanoate (compound 50a)

Dicyclohexylcarbodiimide, DCC (2.44 g) was added at 5° C. to a solution of tert-butyloxycarbonyl Valine, Boc-valine (4.57 g) and 1-hydroxybenzotriazole, HOBt (2.49 g) in 150 mL of THF-AcOEt (2:1). The cooling bath is removed after 5 mn stirring and stirring is pursued at 20° C. for 3 h. The suspension was filtered on a Buchner and the precipitate (DCU) was washed twice with 20 mL AcOEt. The combined filtrates were added to a mixture of compound 13 (6.4 g) and NEt3 (4 mL) in THF 100 mL. Stirring was continued for 3 days. The mixture was washed with 200 mL of 1M $Na_2CO_3$ followed by 100 mL $H_2O$ and 100 mL brine. The solution is concentrated under vacuum below 40° C. The ester 50a is separated on a silica gel column chromatography, using AcOEt-cyclohexane (1:1) as eluent. Yield: 45%. NMR(DMSOd6) δ: 0.75 (3H,t J=6.5 Hz); 1.12 (m, 3H); 1.38 (d, 6H), 1.54 (m, 17H); 1.95 (m, 1H); 3.65 (m, 1H); 4.05 (m, 4H); 4.55 (1H, Hept, J=6.5 Hz); 5.05 and 5.45 (2 brs, 2H); 6.25 (brs, 1H); 7.25 (m, 5H); 7.80 (s, 1H).

[(2R)-2-[[6-[benzyl(ethyl)amino]-9-isopropyl-purin-2-yl]amino]butyl] (2S)-2-amino-3-methyl-butanoate hydrochloride or L-valyl ester of (2R)-2-[[6-[benzyl(ethyl)amino]-9-isopropyl-purin-2-yl]amino]butan-1-ol hydrochloride (compound 50).

The ester 50a was dissolved in anhydrous 50 mL $Et_2O$. A 2 M HCl in $Et_2O$ was added and stirred at 20° C. for 24 h. The solvent was decanted and the solid with triturated with $Et_2O$ (3×20 mL). The precipitate was then dried under vacuum ($P_2O_5$) for 48 h to afford 40. Yield: 43%. NMR (DMSOd6) δ: 0.75 (m, 3H); 1.15 (m, 3H); 1.45 (m 6H), 1.64 (m, 8H); 2.35 (m, 1H); 3.75 (m, 1H); 4.12 (m, 4H); 4.55 (m, 1H); 4.95 and 5.45 (2 brs, 2H); 6.25 (brs, 1H); 7.25 (m, 5H); 8.20 (brs, 1H). 8.45 (m, 3H).

Preparation of compound 49: [(2R)-2-[[9-isopropyl-6-(N-methylanilino)purin-2-yl]amino]butyl] (2S)-2-amino-3-methyl-butanoate hydrochloride or L-valyl ester of (2R)-2-[[9-isopropyl-6-(N-methylanilino)purin-2-yl]amino]butan-1-ol hydrochloride Compound (49) was prepared from Aftin 5 by the same procedure as for Compound 50. The synthesis of compound 49 is depicted in following scheme.

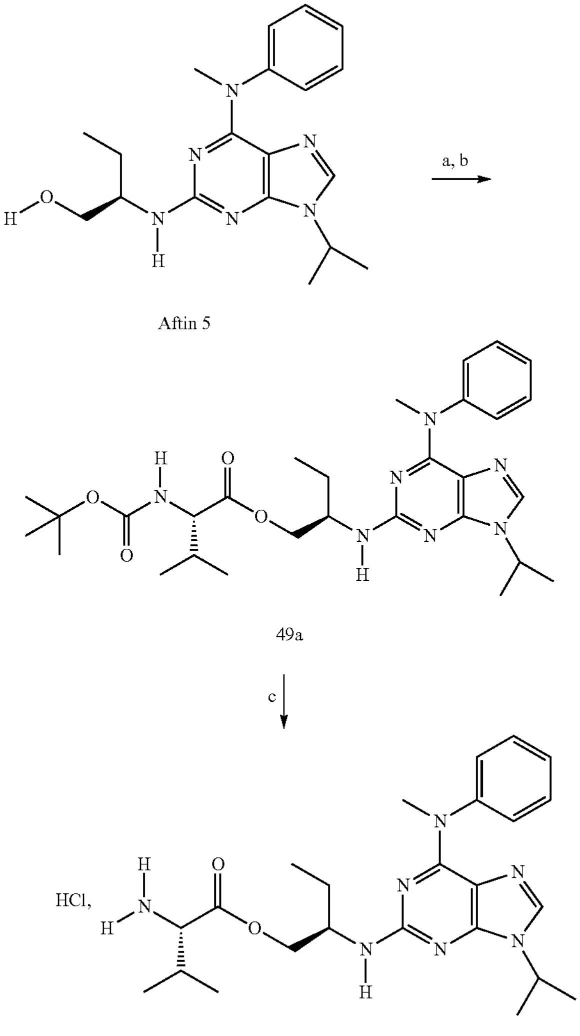

Aftin 5

49a

49

Reagents and conditions. a: Boc-valine, DCC, HOBt. b: Aftin 5, c: HCl, $Et_2O$.

[(2R)-2-[[9-isopropyl-6-(N-methylanilino)purin-2-yl]amino]butyl] (2S)-2-(tert-butoxycarbonylamino)-3-methyl-butanoate (compound 49a).

NMR(DMSOd6) δ: 0.85 (3H,t J=6.5 Hz); 1.35 (d, 6H), 1.45 (m, 15H); 1.92 (m, 1H); 3.73 (s, 3H); 3.75 (m, 1H); 4.05 (m, 3H); 4.55 (1H, Hept, J=6.5 Hz); 6.35 (brs, 1H); 7.28 (m, 5H); 7.75 (s, 1H).

[(2R)-2-[[9-isopropyl-6-(N-methylanilino)purin-2-yl]amino]butyl] (2S)-2-amino-3-methyl-butanoate hydrochloride or L-valyl ester of (2R)-2-[[9-isopropyl-6-(N-methylanilino)purin-2-yl]amino]butan-1-ol hydrochloride (compound 49).

NMR(DMSOd6) δ: 0.95 (3H,t J=6.5 Hz); 1.10 (d, 6H), 1.55(2d, 6H); 2.20 (m, 1H); 3.75 (s, 3H); 3.85 (m, 1H); 4.25 (m, 3H); 4.65 (m, 1H); 6.35 (brs, 1H); 7.45 (m, 5H); 8.20 (brs, 1H). 8.55 (brs, 3H).

The invention claimed is:

1. A method for treating non-traumatic acquired brain injury, wherein the brain injury is caused by oxygen deficiency, in an individual in need thereof, comprising administering an effective amount of a compound of formula (I)

(I)

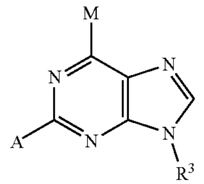

in which

M represents a $NR^1R^2$ group or an $OR^1$ group,

A represents a $NR^4R^5$ group, $R^1$ is an aryl group, or a —$CH_2$-aryl group, said aryl being optionally substituted with one or more substituents independently chosen from a halogen atom, a $CF_3$ group, an $OR^6$ group, an aryl group, a heteroaryl group and a ($C_1$-$C_6$)alkyl group, $R^2$ is a ($C_1$-$C_6$)alkyl group, $R^6$ and $R^7$ represent independently of each other a hydrogen atom or a ($C_1$-$C_6$)alkyl group, $R^3$ is a ($C_1$-$C_6$)alkyl group, a ($C_3$-$C_6$)cycloalkyl group, or a —$CH_2$-aryl group, $R^4$ is a hydrogen atom or a ($C_1$-$C_6$)alkyl group, $R^5$ is a ($C_1$-$C_8$)alkyl group or a ($C_3$-$C_6$)cycloalkyl group, said alkyl and cycloalkyl group being substituted with one or more substituents independently chosen from a hydroxyl group, and a —$OCOR^a$ group, $R^a$ represents a ($C_1$-$C_6$)alkyl group, said alkyl group being substituted by an amino group, or alternatively $R_4$ and $R_5$ may form with the nitrogen atom bearing them a heterocycloalkyl group, said heterocycloalkyl group being selected from the group consisting of morpholinyl, piperidinyl, pyrrolidinyl, piperazinyl and homopiperazinyl groups, and being optionally substituted by one or more substituents independently chosen from a ($C_1$-$C_4$)alkyl group, a $NR^6R^7$ group and a halogen atom, or an addition salt with a pharmaceutically acceptable acid.

2. The method according to claim 1, wherein

M represents a $NR^1R^2$ group, and said $NR^1R^2$ radical is chosen from the following radicals:

(1)

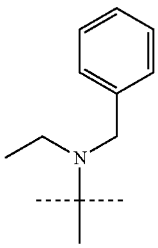

,

-continued (2)

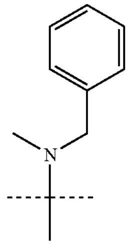, (15)

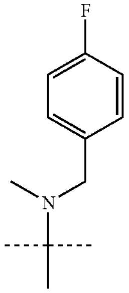, (17)

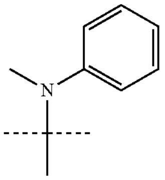, (25)

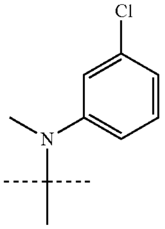, (43)

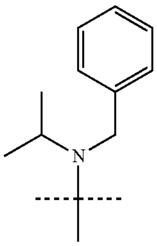 and (44)

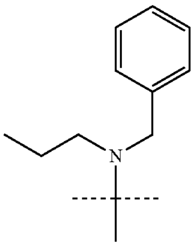, or an addition salt with a pharmaceutically acceptable acid.

3. The method according to claim 1, wherein

A represents a $NR^4R^5$ group, $R^4$ is a hydrogen atom, $R^5$ is a $(C_1-C_8)$ alkyl group, said alkyl group being substituted with one or more substituents independently chosen from, a hydroxyl group and a —$OCOR^a$ group, $R^a$ represents a $(C_1-C_6)$alkyl group, said alkyl group being substituted by an amino group, or alternatively $R^4$ and $R^5$ may form with the nitrogen atom bearing them a heterocycloalkyl group, said heterocycloalkyl group being selected from the group consisting of morpholinyl, piperidinyl, pyrrolidinyl, piperazinyl and homopiperazinyl groups, and being optionally substituted by one or more substituents independently chosen from a $(C_1-C_4)$alkyl group, a $NR^6R^7$ group and a halogen atom, and $R^6$ and $R^7$ represent independently of each other a hydrogen atom or a $(C_1-C_6)$alkyl group, or an addition salt with a pharmaceutically acceptable acid.

4. The method according to claim 1, wherein

A represents a group a $NR^4R^5$ group selected from the following radicals

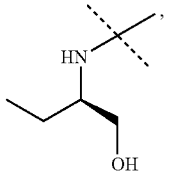, 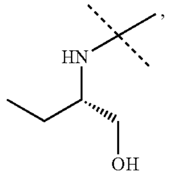, 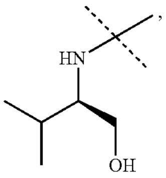

or an addition salt with a pharmaceutically acceptable acid.

5. The method according to claim 1, wherein the compound is selected from compound 13, 14, 15, 18, 20, 23, 26, 31, 38 and Aftin-5 as defined herein after

| No | Structure |
| --- | --- |
| 13 | 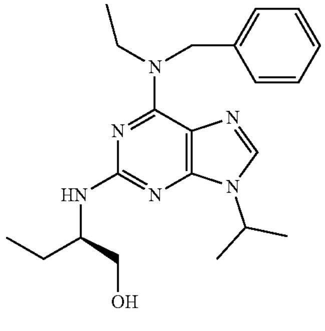 [SMILES: CC[C@H](CO)Nc1nc(N(CC)Cc2ccccc2)c2ncn(C(C)C)c2n1] |
| 14 | 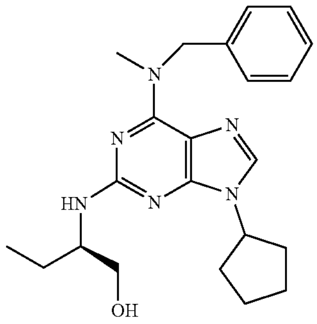 [SMILES: CC[C@H](CO)Nc1nc(N(C)Cc2ccccc2)c2ncn(C3CCCC3)c2n1] |

-continued

| No | Structure |
|---|---|
| 15 | 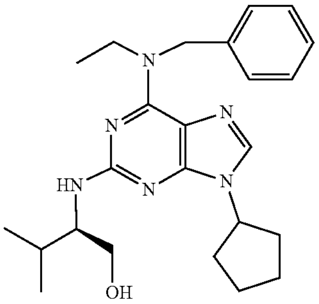 [SMILES: CCN(Cc1ccccc1)c1nc(N[C@@H](CO)C(C)C)nc2c1ncn2C1CCCC1] |
| 18 | 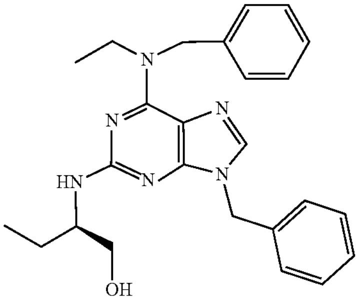 [SMILES: CC[C@H](CO)NC(=N)/N=C(\c1ncn(Cc2ccccc2)c1C)N(CC)Cc1ccccc1] |
| 20 | 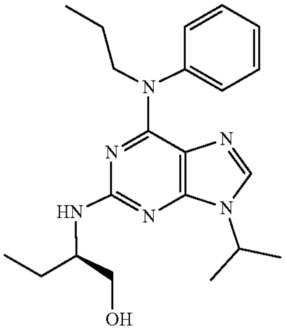 [SMILES: CCCN(c1ccccc1)c1nc(N[C@H](CC)CO)nc2c1ncn2C(C)C] |
| 23 | 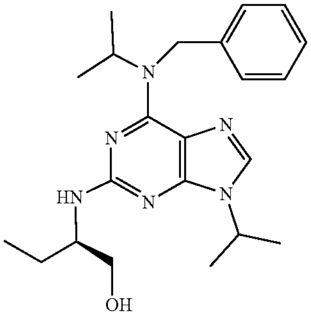 [SMILES: CC[C@H](CO)Nc1nc(N(Cc2ccccc2)C(C)C)c2ncn(C(C)C)c2n1] |
| 26 | 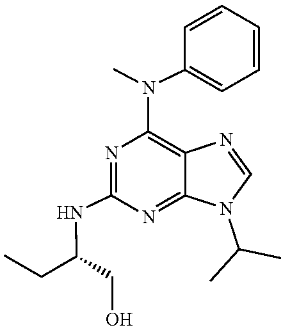 [SMILES: CC[C@@H](CO)Nc1nc(N(C)c2ccccc2)c2ncn(C(C)C)c2n1] |

-continued

| No | Structure |
|---|---|
| 31 | 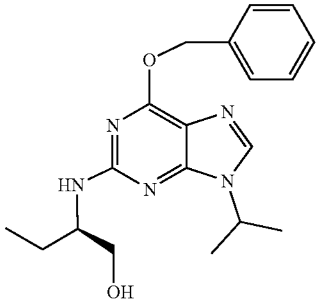 [SMILES: CC[C@H](CO)Nc1nc(OCc2ccccc2)c2ncn(C(C)C)c2n1] |
| 38 | 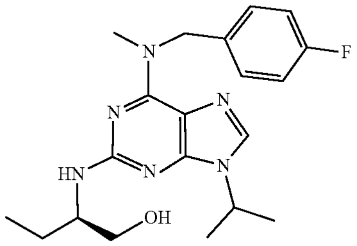 [SMILES: CC[C@H](CO)NC(=N)/N=C(\c1ncn(C(C)C)c1C)N(C)Cc1ccc(F)cc1] |
| Aftin-5 | 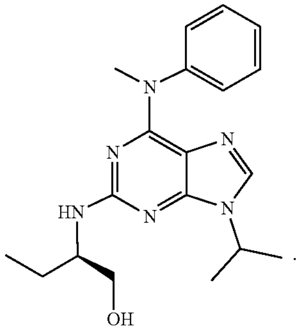 [SMILES: CC[C@H](CO)Nc1nc(N(C)c2ccccc2)c2ncn(C(C)C)c2n1] |

6. The method according to claim 1, wherein the brain injury is caused by hypoxic brain injury/anoxic brain injury, hypoxia-ischemia, hypoxic-ischemic encephalopathy, diffuse cerebral hypoxia, focal cerebral ischemia, cerebral infarction, and global cerebral ischemia.

7. The method according to claim 1, wherein the non-traumatic acquired brain injury is a hypoxic injury.

8. The method according to claim 7, wherein the non-traumatic acquired brain injury is a neonatal encephalopathy, including neonatal hypoxia-ischemia and neonatal hypoxic-ischemic encephalopathy.

9. The method according to claim 1, wherein said compound of formula (I) decreases and/or repairs the brain injury lesions.

* * * * *